US006046381A

United States Patent [19]
Mucke et al.

[11] Patent Number: 6,046,381
[45] Date of Patent: Apr. 4, 2000

[54] APOLIPOPROTEIN E TRANSGENIC MICE AND ASSAY METHODS

[75] Inventors: Lennart Mucke, Foster City; Jacob Raber, San Francisco; Manuel Buttini, Albany; Robert W. Mahley, San Francisco; Robert E. Pitas, Orinda, all of Calif.

[73] Assignee: The Regents of the University of California, Oakland, Calif.

[21] Appl. No.: 09/070,670

[22] Filed: Apr. 30, 1998

[51] Int. Cl.[7] ............................. C12N 5/00; C12N 15/00; C12N 15/85

[52] U.S. Cl. ................................. 800/18; 800/3; 800/13; 800/14; 435/325; 435/455

[58] Field of Search .................................. 435/325, 455; 800/3, 13, 14, 18

[56] References Cited

U.S. PATENT DOCUMENTS

| | | | |
|---|---|---|---|
| 4,983,586 | 1/1991 | Bodor | 514/58 |
| 5,002,935 | 3/1991 | Bodor | 514/58 |
| 5,017,566 | 5/1991 | Bodor | 514/58 |
| 5,153,179 | 10/1992 | Eibl | 514/34 |

FOREIGN PATENT DOCUMENTS

| | | |
|---|---|---|
| WO 94/13798 | 6/1994 | WIPO . |
| WO 95/06456 | 3/1995 | WIPO . |
| WO 95/06470 | 3/1995 | WIPO . |

OTHER PUBLICATIONS

Alberts, Mark J., et al., "ApoE Genotype and Survival from Intracerebral Haemorrhage", *The Lancet* (1995) 346:575.

Beffert, U., et al., "Apolipoprotein E Uptake is Increased in the Presence of Beta Amyloid Peptides and Reduced by Blockade of the Low Density Lipoprotein Receptor", *Society for Nueroscience* (1995) 21:6 (Abstract No. 9.6).

Bellosta et al., "Stable Expression and Secretion of Apolipoprotein E3 and E4 in Mouse Neuroblastoma Cells Produces Differential Effects on Neurite Outgrowth", *J. Biol. Chem.* (1995) 270(45):27063–27071.

Boyles et al., "Apolipoprotein E Associated with Astrocytic Glia of the Central Nervous System and with Nonmyelinating Glia of the Peripheral Nervous System", *J. Clin. Invest.* (1985) 76:1501–1513.

Corder et al., "Gene Dose of Apolipoprotein E Type 4 Allele and the Risk of Alzheimer's Disease in Late Onset Families", *Science* (1993) 261:921–923.

Crowther, "Tau Protein and Paired Helical Filaments of Alzheimer's Disease", *Curr. Opin. Struct. Biol.* (1993) 3:202–206.

Dong et al., "Apolipoprotein E4 Preference for Very Low Density Lipoproteins Results from Domain Interaction Mediated by Glutamic Acid–255 and Arginine–61", *Circulation* (1995) 92(8):I–427–I–428 (Abstract No. 2040).

Dong et al., "Human Apolipoprotein E: Role of Arginine 61 in Mediating the Lipoprotein Preferences of the E3 and E4 Isoforms", *J. Biol. Chem.* (1994) 269(35):22358–22365.

Elshourbagy et al., "Apolipoprotein E mRNA is Abundant in the Brain and Adrenals, as Well as in the Liver, and is Present in Other Peripheral Tissues of Rats and Marmosets", *Proc. Natl. Acad. Sci. USA* (1985) 82:203–207.

Feskens et al., "Apolipoprotein E4 Alleles an d Cognitive Decline in Elderly Men", *BMJ* (1994) 309:1202–1206.

Forss–Petter et al., "Transgenic Mice Expressing β–Galactosidase in Mature Neurons Under Neuron–Specific Enolase Promoter Control", *Neuron* (1990) 5:187–197.

Handelmann et al., "Effects of Apolipoprotein E, β–Very Low Density Lipoproteins, and Cholesterol on the Extension of Neurites by Rabbit Dorsal Root Ganglion Neurons in Vitro", *J. Lipid Res.* (1992) 33:1677–1688.

Helkala et al., "The Association of Apolipoprotein E Polymorphism with Memory: A Population Based Study", *Neurosci. Letts.* (1995) 191:141–144.

Holtzman et al., "LRP Mediates Apolipoprotein E–Dependent Neurite Outgrowth in a CNS–Derived Neuronal Cell Line", *Soc. Neurosci.* (1995) 21:1009 (Abstract No. 400.10).

Ignatius et al., "Expression of Apolipoprotein E During Nerve Degeneration and Regeneration", *Proc. Natl. Acad. Sci. USA* (1986) 83:1125–1129.

Innerarity et al., "Binding of Arginine–Rich (E) Apoprotein after Recombination with Phospholipid Vesicles to the Low Density Lipoprotein Receptors of Fibroblasts", *J. Biol. Chem.* (1979) 254:4186–4190.

Innerarity et al., "The Receptor–Binding Domain of Human Apolipoprotein E", *J. Biol. Chem.* (1983) 258:12341–12347.

Jackowski, Andres, "Neural Injury Repair: Hope for the Future as Barriers to Effective CNS Regeneration Become Clearer", *British Journal of Neurosurgery* (1995) 9:303–317.

Ji et al., "Secretion–Capture Role for Apolipoprotein E in Remnant Lipoprotein Metabolism Involving Cell Surface Heparan Sulfate Proteoglycans", *J. Biol. Chem.* (1994) 269:2764–2772.

Lawn, "Lipoprotein in Heart Disease", *Scientific American* (1992) pp. 54–60.

Ma, J., et al., "Promotion of the Neurotoxicity of Alzheimer Aβ Protein by the Pathological Chaperones Act and ApoE4: Inhibition by Aβ–Related Peptides and ApoE2", *Society for Neuroscience* (1995) 21:1714 (Abstract No. 670.7).

(List continued on next page.)

*Primary Examiner*—Deborah Crouch
*Assistant Examiner*—Anne-Marie Baker
*Attorney, Agent, or Firm*—Dianna L. DeVore; Bozicevic, Field & Francis LLP

[57] ABSTRACT

The present invention features non-human transgenic animal models for gene function, wherein the transgenic animal is characterized by having altered endogenous apolipoprotein E gene function and a transgene for an exogenous human apolipoprotein E isoform. The transgenic animals may be either homozygous or heterozygous for the transgene. The invention also features methods for using non-human transgenic animal models for the study of apolipoprotein E-mediated pathologies and the identification of compounds and therapies for such pathologies.

11 Claims, 8 Drawing Sheets

OTHER PUBLICATIONS

Mahley, "Apolipoprotein E: Cholesterol Transport Protein with Expanding Role in Cell Biology", *Science* (1988) 240:622–630.

Muller et al., "A Specific 37,000–Dalton Protein that Accumulates in Regenerating but Not in Nonregenerating Mammalian Nerves", *Science* (1985) 228:499–501.

Nathan et al., "The Inhibitory Effect of Apolipoprotein E4 on Neurite Outgrowth is Associated with Microtubule Depolymerization", *J. Biol. Chem.* (1995) 270:19791–19799.

Nathan et al., "Differential Effects of Apolipoproteins E3 and E4 on Neuronal Growth in Vitro", *Science* (1994) 264:850–852.

Nathan et al., "Apolipoprotein E3 and E4–Induced Differences in Neurite Outgrowth are Associated with Differences in the Subcellular Localization of Apolipoprotein E", *Soc. Neurosci.* (1994) 20(Part 2):1033 (Abstract).

Petersen et al., "Apolipoprotein E Status as a Predictor of the Development of Alzheimer's Disease in Memory–Impaired Individuals", *JAMA* (1995) 273:1274–1278.

Pitas et al., "Astrocytes Synthesize Apolipoprotein E and Metabolize Apolipoprotein E–Containing Lipoproteins", *Biochimica et Biophysica Acta* (1987) 917:148–161.

Pitas et al., "Cell Surface Receptor Binding of Phospholipid Protein Complexes Containing Different Ratios of Receptor–Active and –Inactive E Apoprotein", *J. Biol. Chem.* (1980) 255:5454–5460.

Pitas et al., "Lipoproteins and Their Receptors in the Central Nervous System: Characterization of the Lipoproteins in Cerebrospinal Fluid and Identification of Apolipoprotein B,E(LDL) Receptors in the Brain", *J. Biol. Chem.* (1987) 262:14352–14360.

Quon et al., "Formation of β–Amyloid Protein Deposits in Brains of Transgenic Mice", *Nature* (1991) 352:239–241.

Reed et al., "Lower Cognitive Performance in Normal Older Adult Male Twins Carrying the Apolipoprotein E ε 4 Allele", *Arch. Neurol.* (1994) 51:1189–1192.

Roheim et al., "Apolipoproteins in Human Cerebrospinal Fluid", *Proc. Natl. Acad. Sci. USA* (1979) 76:4646–4649.

Rudinger, J., "Characteristics of the Amino Acid as Components of a Peptide Hormone Sequence", *Peptide Hormones* (1976) ed. J.A. Parsons, University Park Press, Baltimore, pp. 1–7.

Saunders et al., "Association of Apolipoprotein E Allele ε4 with Late–Onset Familial and Sporadic Alzheimer's Disease", *Neurol.* (1993) 43:1467–1472.

Selkoe, " The Molecular Pathology of Alzheimer's Disease", *Neuron* (1991) 6:487–498.

Strittmatter et al., "Hypothesis: Microtubule Instability and Paired Helical Filament Formation in the Alzheimer Disease Brain are Related to Apolipoprotein E Genotype", *Exp. Neurol.* (1994) 125:163–171.

Weisgraber et al., "The Role of Apolipoprotein E in the Nervous System", *Curr. Opin. Lipidol.* (1994) 5:110–116.

Weisgraber, Karl H., et al., "Lipoproteins, Neurobiology, and Alzherimer's Disease: Structure and Function of Apolipoprotein E", *Current Opinion in Structural Biology* (1994) 4:507–515.

Campbell and Wilmut Totipotency and multipotentiality of cultured cells: Applications and progress. Theriogenology 47: 63–72, Jan. 1997.

Hammer et al. Spontaneous inflammatory disease in transgenic rats expressing HLA–B27 and human b2m: An animal model o f HLA–B27–associated disorders. Cell 63: 1099–1112, Nov. 1990.

Mullins et al. Fulminant hypertension in transgenic rats harboring the mouse Ren–2 gene. Nature 344: 541–544, Apr. 1990.

Mullins et al. Expression of the DBA/2J Ren–2 gene in the adrenal gland of transgenic mice. EMBO J. 8: 4065–4072, 1989.

Taurog et al. HLA–B27 inbred and non–inbred transgenic mice. J. Immunol. 141: 4020–4023, Dec. 1988.

Wall, RJ Transgenic livestock: Progress and prospects for the future. Theriogenology 45: 57–68, 1996.

APOLIPOPROTEIN E TRANSGENIC MICE AND ASSAY METHODS

FIELD OF THE INVENTION

The invention relates generally to the field of non-human, transgenic animals altered with respect to the expression of human apolipoprotein E isoform and to assays for determining the effects of compounds on activity modulated by apoE.

BACKGROUND OF THE INVENTION

Apolipoprotein E (ApoE) is a 34,000 molecular weight protein which is the product of a single gene on chromosome 19. Human ApoE exists in three major isoforms designated apoE2, apoE3 and apoE4 (for review, see Mahley (in press) *Molecular and Genetic Bases of Neurological Disease* 2nd ed.; and Mahley *Science* 240:622–630 (1988)). The different isoforms result from amino acid substitutions at amino acid residue positions 112 and 158. The common isoform, apoE3, has a cysteine residue at position 112 and an arginine residue at position 158. The apoE4 isoform differs from apoE3 only at position 112, which is an arginine residue. The apoE2 isoform, associated with type III hyperlipoproteinemia (Mahley (1988)), differs from apoE3 only at position 158, which is a cysteine residue. ApoE3 and apoE4 bind normally to the low density lipoprotein (LDL) receptor, whereas apoE2 does not.

ApoE contains two structural domains, an amino-terminal and a carboxy-terminal domain, each associated with a specific function. Weisgraber *Adv. Protein Chem.* 45:249–302 (1994). The amino terminal domain contains the lipoprotein receptor binding region and the carboxy-terminal domain contains the major lipid-binding elements. The two domains appear to interact with each other in an isoform-specific manner such that amino acid substitutions in one domain influence the function of the other domain, a phenomenon referred to as domain interaction. Domain interaction is responsible for the preference of apoE4 for very low density lipoproteins (VLDL) contrasted with the preference of apoE3 for high density lipoproteins (HDL). The specific amino acid residues in apoE4 that are involved in this interaction are arginine-61 in the amino-terminal domain and glutamic acid-255 in the carboxy-terminal domain. Dong et al. *J. Biol. Chem.* 269:22358–22365 (1994); and Dong and Weisgraber *Circulation* 92:I-427-I-428 (1995)(abstract).

By redistributing lipids among the cells of different organs, apoE plays a critical role in lipid metabolism. While apoE exerts this global transport mechanism in chylomicron and VLDL metabolism, it also functions in the local transport of lipids among cells within a tissue. Cells with excess cholesterol and other lipids may release these substances to apoE-lipid complexes or to HDL containing apoE, which can transport the lipids to cells requiring them for proliferation or repair. The apoE on these lipoprotein particles mediates their interaction and uptake via the LDL receptor or the LRP.

ApoE also functions in a neurobiological role. ApoE mRNA is abundant in the brain, where it is synthesized and secreted primarily by astrocytes. Elshourbagy et al. *Proc. Natl. Acad. Sci. USA* 82:203–207 (1985); Boyles et al. *J. Clin. Invest.* 76:1501–1513 (1985); and Pitas et al. *Biochem. Biophys. Acta* 917:148–161 (1987). The brain is second only to the liver in the level of apoE mRNA expression. ApoE-containing lipoproteins are found in the cerebrospinal fluid and appear to play a major role in lipid transport in the central nervous system (CNS). Pitas et al. *J. Biol. Chem.* 262:14352–14360 (1987). In fact, the major cerebrospinal fluid lipoprotein is an apoE-containing HDL. ApoE promotes marked neurite extension in dorsal root ganglion cells in culture. Handelmann et al. *J. Lipid Res.* 33:1677–1688 (1992). ApoE levels dramatically increase (about 250-fold) after peripheral nerve injury. Mëller et al. *Science* 228:499–501 (1985); and Ignatius et al. *Proc. Natl. Acad. Sci. USA* 83:1125–1129 (1986). ApoE appears to participate both in the scavenging of lipids generated after axon degeneration and in the redistribution of these lipids to sprouting neurites for axon regeneration and later to Schwann cells for remyelination of the new axons. Boyles et al. *J. Clin. Invest.* 83:1015–1031 (1989); and Ignatius et al. *Science* 236:959–962 (1987).

More recently, apoE has been implicated in Alzheimer's disease (hereafter "AD") and cognitive performance. Saunders et al. *Neurol.* 43:1467–1472 (1993); Corder et al. *Science* 261:921–923 (1993); and Reed et al. *Arch. Neurol.* 51:1189–1192 (1994). ApoE4 is associated with the two characteristic neuropathologic lesions of AD: extracellular neuritic plaques representing deposits of amyloid beta (AJ) peptide; and intracellular neurofibrillary tangles representing filaments of hyperphosphorylated tau, a microtubule-associated protein. For review, see, McKhann et al. *Neurol.* 34:939–944 (1984); Selkoe *Neuron* 6:487–498 (1991); Crowther *Curr. Opin. Struct. Biol.* 3:202–206 (1993); Roses *Curr. Neurol.* 14:111–141 (1994); Weisgraber et al. *Curr. Opin. Lipidol.* 5:110–116 (1994); and Weisgraber et al. *Curr. Opin. Struct. Biol.* 4:507–515 (1994).

AD is generally divided into three categories: early-onset familial disease (occurring before 60 years of age and linked to genes on chromosomes 21 and 14); late-onset familial disease; and sporadic late-onset disease. Both types of late-onset disease have recently been linked to chromosome 19 at the apoE locus. Other results suggest that apoE4 is directly linked to the severity of the disease in late-onset families. Roses (1994). Recently, cholesterol lowering drugs, the statins, have been suggested for use in treating AD by lowering apoE4 levels. WO 95/06470.

The neurofibrillary tangles, which are paired helical filaments of hyperphosphorylated tau, accumulate in the cytoplasm of neurons. Tau is a microtubule-associated phosphoprotein which normally participates in microtubule assembly and stabilization; however, hyperphosphorylation impairs its ability to interact with microtubules. Increased binding of tau by apoE has been suggested as a treatment for AD. WO 95/06456.

In vitro tau interacts with apoE3, but not with apoE4. Strittmatter et al. *Exp. Neurol.* 125:163–171 (1994). The interaction of apoE3 with tau may prevent its hyperphosphorylation, thus allowing it to function normally in stabilizing microtubular structure and function. In the presence of apoE4, tau could become hyperphosphorylated and thus inactive, which could promote the formation of neurofibrillary tangles.

ApoE4 has recently been associated with decreased learning ability and impaired memory. Helkala et al. *Neurosci. Letts.* 191:141–144 (1995). ApoE4 has been found to be a strong predictor of the outcome of patients designated as having memory impairment. Note that, apoE4 has been described as a risk factory, rather than a diagnostic. Peterson et al. *JAMA* 273:1274–1278 (1995); and Feskens et al. *BMJ* 309:1202–1206 (1994).

ApoE3 and apoE4 are also though to play a role in neurite repair and remodeling in the CNS. In cultured neurons, apoE3 stimulates neurite extension, whereas apoE4 inhibits neurite extension. Nathan et al., 1994. Repair and remodeling of neurons in response to stress or injury, either chronic or acute, should thus proceed more effectively in the presence of apoE3 than in the presence of apoE4.

There are currently no effective therapies for arresting (and, more importantly, reversing) the impairment of central and peripheral nervous system function once a degenerative cascade begins. Likewise, there is no current therapy for restoration of normal, central and peripheral nervous system function when the induced stress has a less catastrophic or partially reversible effect compared to the dementias. The effects of events that impair the function of the CNS, such as traumatic brain injury and stroke are in need of such therapies to mitigate or reverse the resulting damage. In addition, no effective therapies for reducing or reversing impairment in cognitive learning and behavior are known, as relatively little is understood about the mechanisms of cognitive learning and memory.

SUMMARY OF THE INVENTION

The present invention comprises non-human transgenic animal models for the study of apolipoprotein E-mediated pathologies, wherein the transgenic animal is characterized by 1) partial or complete loss of function of endogenous apoE gene or genes and/or 2) introduction of exogenous apoE transgenes, e.g., human apoE. The transgenic animals may be either homozygous or heterozygous for these alterations. Preferably, the human transgene expresses either apoE3 or apoE4. The invention includes cells with the combination of apoE loss and exogenous apoE genes, e.g., human transgene. These cells may be from animals with a native genotype, or from animals which have been engineered independently.

A method of screening for biologically active agents by examining behavioral phenomena of animal models of the present invention is disclosed. Animal models may have a complete of partial knockout of the endogenous apoE gene, an exogenous and stably transmitted exogenous apoE transmitted apoE sequence, an apoE promoter sequence linked to a reporter construct, or any combination of these. The phenomena measured may include cognitive function, such as spatial learning, and in particular may identify effects that are gender dependent. Alternatively, or in conjunction, the phenomena examined may be examining phenotypes such as neurodegeneration, and in particular neurodegeneration that is age-dependent. The screening methods are of particular use for determining the specificity and action of drugs that may interact with apoE receptors, and particularly drugs that affect central and peripheral nervous system function.

Another aspect of the invention comprises a method of screening compounds for specificity of action on apolipoprotein E isoform function by combining a candidate agent with a non-human transgenic animal having a complete or partial knockout of endogenous apoE gene, an exogenous and stably transmitted exogenous apoE transmitted apoE sequence, an apoE promoter sequence linked to a reporter construct, or any combination of these. Agents that affect apoE are determined by examining apoE function and/or expression. Preferably, levels and/or function of human apoE3 or apoE4 are examined.

A primary object of the invention is to provide a method of using a transgenic animal model for identifying candidate agents (e.g., a small molecule drug or an endogenous factory) that alter behavior associated with disorders of the peripheral and/or central nervous system. Such methods are useful for screening candidate agents for use in treating or relieving the symptoms of apoE-related pathologies. The cells derived therefrom are also useful for screening biologically active agents that may modulate apoE function.

Another object is to provide a method of using a transgenic animal model to examine potential apoE-mediated side effects of agents that affect the central or peripheral nervous system. Such methods are useful for determining potential negative long-term effects in agents used in the treatment of peripheral and/or central nervous system disorders.

Another object is to provide a means for studying apoE-mediated activity using an animal model. The animals are useful as a model to investigate the role of apoE both in pathologies, both acute and chronic, and in normal brain function.

An advantage of the claimed invention is that the transgenic animal models used in the methods as described herein exhibit phenomena associated with changes in the peripheral and/or central nervous system that can be modulated by the introduction of exogenous genetic sequences. The exogenous genetic sequence may express a gene from the same species as the animal model, or preferably a human gene.

Another advantage of the claimed invention is that the transgenic animal models can be used to study human pathologies modulated by the altered expression of a single apoE isoform.

Another advantage of the claimed invention is that the transgenic animal models can be used to study models of acute trauma such as cerebral ischemic injury, other traumatic cerebral injury, and/or peripheral nerve damage.

These and other objects, advantages and features of the present invention will become apparent to those persons skilled in the art upon reading the details of the invention more fully set forth below.

DATABASE REFERENCES FOR GENETIC SEQUENCES

Figure 1:
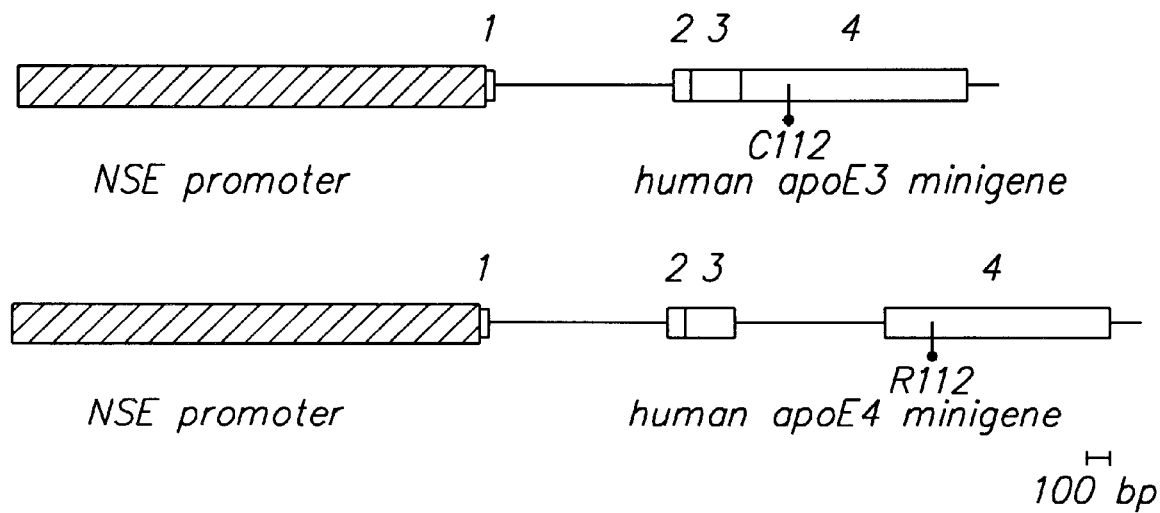
FIG. 1 is a block diagram illustrating the structure of the NSE-apoE transgenes.

The human apolipoprotein E3 gene has the Genbank accession number E08423. The human apolipoprotein E4 gene has the Genbank accession number M10065. The mouse apolipoprotein E gene has the Genbank accession number D00466.

DESCRIPTION OF THE SPECIFIC EMBODIMENTS

Non-human transgenic animal models useful for screening drugs or candidate drugs are provided. The animals have a genetically altered endogenous apolipoprotein E (hereafter "apoE") gene and an introduced exogenous human apoE gene. Alterations to the non-human gene include deletion or other loss of function mutations, introduction of an exogenous gene having a nucleotide sequence with targeted or random mutations, or a combination thereof. The transgenic animals may be either homozygous or heterozygous for the genetic alteration.

The subject animals are useful for testing the actions of drugs and candidate drugs developed to modulate human apoE activity. Completely selective compounds will interact with apoE in an isoform-dependent manner, and thus will affect only the intended apoE isoform. In addition, these animals provide a useful model for the behavioral testing of anti-apoE compounds. The animals are also used to determine the extent to which apoE contributes to the efficacy of drugs in current use.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and," and "the" include plural referents unless the context clearly dictates otherwise. Thus, for example, reference to "a construct" includes a plurality of such constructs and reference to "the apolipoprotein E-encoding nucleic acid" includes reference to one or more apolipoprotein E-encoding nucleic acids and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing here is to be construed as an admission that the inventors are not entitled to antedate such disclosure by virtue of prior invention. Further, the publication dates provided may be different from the actual publication date which may require independent verification.

DEFINITIONS

The term "transgene" is used herein to describe genetic material which has been or is about to be artificially inserted into the genome of a cell, particularly a mammalian cell for implantation into a living animal.

By "Alzheimer's disease" (abbreviated herein as "AD") is meant a condition associated with formation of neuritic plaques comprising amyloid β protein primarily in the hippocampus and cerebral cortex, as well as impairment in both learning and memory. "AD" as used herein is meant to encompass both AD as well as AD-type pathologies, i.e., diseases of the central nervous system with symptoms similar to AD.

By "symptoms similar to AD" and "phenomenon associated with AD" is meant a structural, molecular, or functional event associated with AD, particularly such an event that is readily assessable in an animal model. Such events include, but are not limited to, amyloid deposition, neuropathological developments, learning and memory deficits, and other AD-associated characteristics.

By "β amyloid deposit" is meant a deposit in the brain composed of β amyloid as well as other substances.

By "transformation" is meant a permanent or transient genetic change, preferably a permanent genetic change, induced in a cell following incorporation of new DNA (i.e., DNA exogenous to the cell). Where the cell is a mammalian cell, a permanent genetic change is generally achieved by introduction of the DNA into the genome of the cell.

By "transgenic animal" is meant a non-human animal, usually a mammal (e.g., a mouse, rat, rabbit, hamster, etc.), having a non-endogenous (i.e., heterologous) nucleic acid sequence present as an extrachromosomal element in a portion of its cell or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

A "knock-out" of a gene means an alteration in the sequence of the gene or sequence associated with the gene that results in a decrease of function of the target gene, preferably such that target gene expression is undetectable or insignificant. A knock-out of an endogenous apoE gene means that function of the apoE gene has been substantially decreased so that expression is not detectable or only present at insignificant levels. "Knock-out" transgenics can be transgenic animals having a heterozygous knock-out of the apoE gene or a homozygous knock-out of the apoE gene. "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

By "construct" is meant a recombinant nucleic acid sequence, generally recombinant DNA sequences, generated for the purpose of the expression of a specific nucleotide sequence(s), or is to be used in the construction of other recombinant nucleotide sequences.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that a nucleotide sequence of interest is positioned adjacent a nucleotide sequence that directs transcription and translation of the introduced nucleotide sequence of interest (i.e., facilitates the production of, e.g., a polypeptide encoded by an apoE sequence).

TRANSGENIC ANIMALS

The term "transgene" is used herein to describe genetic material that has been or is about to be artificially inserted into the genome of a cell, particularly a mammalian cell for implantation into a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

Transgenic animals comprise an exogenous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

In the present invention, transgenic knockouts have a partial or complete loss of function in one or both alleles of the endogenous apoE gene.

Preferably, the target gene expression is undetectable or insignificant. A knock-out of an endogenous apoE gene means that function of the apoE protein has been substantially decreased so that expression is not detectable or only present at insignificant levels. This may be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. In some cases the exogenous transgene sequences are ultimately deleted from the genome, laving a net change to the native sequence. Different approaches may be used to achieve the "knock-out". See U.S. Pat. Nos. 5,464,764, 5,627,059 and related patents and publications to Capecchi et al. A chromosomal deletion of all or part of the native gene may be induced, including deletions of the non-coding regions, particularly the promoter region, 3' regulatory sequences, enhancers, or deletions of gene that activate expression of apoE genes. A functional knock-out may also be achieved by the introduction of an anti-sense construct that blocks expression of the native genes (for example, see Li and Cohen Cell 85:319–329 (1996)). "Knock-outs" also include conditional knock-outs, for example where alteration of the target gene occurs upon exposure of the animal to a substance that promotes target gene alteration, introduction of an enzyme that promotes recombination at the target gene site (e.g., Cre in the Cre-lox system), or other method for directing the target gene alteration postnatally.

The exogenous apoE gene is human and may be a wild-type gene, a naturally occurring polymorphism, or a genetically manipulated sequence, for example having deletions, substitutions or insertions in the coding or non-coding regions. The introduced sequence may encode a apoE polypeptide, or may utilize the apoE promoter operably linked to a reporter gene. Where the introduced gene is a coding sequence, it is usually operably linked to a promoter, which may be constitutive or inducible, and other regulatory sequences required for expression in the host animal. By "operably linked" is meant that a DNA sequence and a regulatory sequence(s) are connected in such a way as to permit gene expression when the appropriate molecules, e.g. transcriptional activator proteins, are bound to the regulatory sequence(s).

Specific constructs of interest include, but are not limited to, anti-sense apoE, which will block native apoE expression, expression of dominant negative apoE mutations, and over-expression of a apoE gene. A detectable marker, such as lac Z may be introduced into the locus, where upregulation of expression will result in an easily detected change in phenotype. Constructs utilizing the apoE promoter region, in combination with a reporter gene or with the coding region are also of interest.

A series of small deletions and/or substitutions may be made in the apoE gene to determine the role of different exons in DNA binding, transcriptional regulation, etc. By providing expression of apoE protein in cells in which it is otherwise not normally produced, one can induce changes in cell behavior.

DNA constructs for homologous recombination will comprise at least a portion of the apoE gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. *Methods in Enzymology* 185:527–537 (1990).

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factory (LIF). When ES cells have been transformed, they may be used to produce transgenic animals. See U.S. Pat. Nos. 5,387,742, 4,736,866 and 5,565,186 for methods of making transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allergenic or congenic grafts or transplants, or in in vitro culture.

apoE NUCLEIC ACID COMPOSITIONS

The terms "apolipoprotein E" and "apoE" are used generically to designate apoE genes, e.g. homologs from rat, human, mouse, guinea pig, etc., and their alternate forms. Used generically, this term encompasses different isoforms of apoE as well, including human apoE3 and apoE4. The term is also intended to means the open reading frame encoding specific polypeptides, introns, and adjacent 5' and 3' non-coding nucleotide sequences involved in the regulation of expression, up to about 1 kb beyond the coding region, but possibly further in either direction. The DNA sequences encoding apoE may be cDNA or genomic DNA or a fragment thereof. The gene may be introduced into an appropriate vector for extrachromosomal maintenance or for integration into the host.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kb or smaller; and substantially free of flanking chromosomal sequence.

The sequence of this 5' region, and further 5' upstream sequences and 3' downstream sequences, may be utilized for promoter elements, including enhancer binding sites, that provide for expression in tissues where apoE is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. *Mol Med* 1:194–205 (1995); Mortlock et al. *Genome Res.* 6:327–33 (1996); and Joulin and Richard-Foy *Eur J Biochem* 232:620–626 (1995).

The regulatory sequences may be used to identify cis acting sequences required for transcriptional or translational regulation of apoE expression, especially in different tissues or stages of development, and to identify cis acting sequences and trans acting factors that regulate or mediate expression. Such transcription or translational control regions may be operably linked to an apoE gene in order to promote expression of wild type or altered apoE or other proteins of interest in cultured cells, or in embryonic, fetal or adult tissues, and for gene therapy.

The nucleic acid compositions used in the subject invention may encode all or a part of the apoE polypeptides as appropriate. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used.

Homologs of cloned apoE are identified by various methods known in the art. Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identify may be determined by hybridization under stringent conditions, for example, at 50° C. or higher and 0.1×SSC (9 mM saline/0.9 mM sodium citrate). By using probes, particularly labeled probes of DNA sequences, one can isolate homologous or related genes. The source of homologous genes may be any species, e.g. primate, rodents, canines, felines, bovines, ovines, equines, etc.

The apoE sequence, including flanking promoter regions and coding regions, may be mutated in various ways known in the art to generate targeted changes in promoter strength, sequence of the encoded protein, etc. The sequence changes may be substitutions, insertions or deletions. Deletions may include large changes, such as deletions of a domain or exon. Other modifications of interest include epitope tagging, e.g. with the FLAG system, HA, etc. For studies of subcellular localization, fusion proteins with green fluorescent proteins (GFP) may be used. Such mutated genes may be used to study structure-function relationships of apo polypeptides, or to alter properties of the proteins that affect their function or regulation.

Techniques for in vitro mutagenesis of cloned genes are known. Examples of protocols for scanning mutations may be found in Gustin et al., *Biotechiques* 14:22 (1993); Barany, *Gene* 37:111–23 (1985); Colicelli et al., *Mol Gen Genet* 199:537–9 (1985); and Prentki et al., *Gene* 29:303–13 (1984). Methods for site specific mutagenesis can be found in Sambrook et al., *Molecular Cloning: A Laboratory Manual,* CSH Press, pp. 15.3–15.108 (1989); Weiner et al., *Gene* 126:35–41 (1993); Sayers et al., *Biotechniques* 13:592–6 (1992); Jones and Winistorfer, *Biotechniques* 12:528–30 (1992); Barton et al., *Nucleic Acids Res* 18:7349–55 (1990); Marotti and Tomich, *Gene Anal Tech* 6:67–70 (1989); and Zhu Anal Biochem 177:120–4 (1989).

DRUG SCREENING ASSAYS

Through use of the subject transgenic animals or cells derived therfrom, one can identify compounds that bind to, modulate, enhance or repress apoE activity. Screening to determine drugs that lack effect on these proteins is also of interest. Areas of investigation are the development of anti-degenerative or cognitive therapies. Of particular interest are screening assays for agents that have a low toxicity for human cells. Assays of the invention make it possible to identify compounds which ultimately (1) have a positive affect on nerve cell growth and as such are therapeutics or (2) have an adverse affect on nerve cell growth and as such should be avoided in products consumed by animals and in particular humans.

A wide variety of assays may be used for this purpose, including in vivo behavioral studies, determination of the localization of drugs after administration, labeled in vitro protein-protein binding assays, protein-DNA binding assays, electrophoretic mobility shift assays, immunoassays for protein binding, and the like. Depending on the particular assay, whole animals may be used, or cells derived therefrom. Cells may be freshly isolated from an animal, or may be immortalized in culture. Cells of particular interest include neural and brain tissue of transgenic animals of the invention. The assays may also measure response to acute injury, i.e. examining the neurite growth, repair and remodelling. Compounds which stimulate neurite extension in vivo are likely to promote nerve regeneration or the formation of synaptic connections during neuronal remodeling in both the central and peripheral nervous system.

The term "agent" as used herein describes any molecule, e.g. protein or non-protein organic pharmaceutical, with the capability of affecting any of the biological actions of apoE. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon on heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modelling.

Screening may be directed to known pharmacologically active compounds and chemical analogs thereof, or to new agents with unknown properties such as those created through rational drug design. Candidate agents for arresting and/or reversing dementia, neuron remodeling, or recovery from acute insults to the nervous system can be screened for their ability to modulate apo E function or phenotypes associated with apoE. For example, a candidate agent for the treatment of age-dependent dementia can be used to treat a mammal with an apoE knockout. Efficacious candidates can be identified by phenotype, i.e. an arrest or reversal of particular cognitive behaviors in comparison with wild-type animals and/or apoE knockout animals expressing exogenous human apoE4. Candidates may also be identified by an enhanced effect in endogenous apoE knockout animals expressing an exogenous human apoE3 transgene. In another example, a candidate agent for the treatment of impaired learning function can be identified by an increase in learned behavior function following treatment in either an endogenous apoE knockout mouse, or an apoE knockout mouse expressing the human apoE4 transgene. Alternatively, candidate agents may be identified by their ability to enhance the activity of exogenous human apoE3.

Screening may also determine if an agent for a different use has an unintended adverse effect on apoE-related functions, including but not limited to neuronal remodeling, repair and recovery from acute insults. For example, certain classes of pharmaceutical agents widely used to treat behavior problems in people with dementia may actually worsen their mental decline. Neuroleptic agents such as chlorpromazine, haloperidol and thioridazine are widely used to treat behavior problems in patients with various forms of dementia, including AD. Recent studies suggest that these drugs may in fact worsen the cognitive or any other function of people treated with these agents. Therapeutic agents such as neuroleptic drugs can be subjected to the methods of the present invention to determine if they are in fact having a detrimental effect on cognitive or any other function by modulation of an apolipoprotein E isoform. This screening can be used for any agent predicted to affect cognitive function to determine if the agent may inadvertently have an unintended effect on apolipoprotein E isoform function.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Antibodies specific for apoE polymorphisms may be used in screening immunoassays, particularly to detect the binding of substrates to apoE isoforms, or to confirm the absence or presence of a apoE receptor in a cell or sample. Samples, as used herein, include biological fluids such as tracheal lavage, blood, cerebrospinal fluid, tears, saliva, lymph, dialysis fluid and the like; organ or tissue culture derived fluids, and fluids extracted from physiological tissues. Also included in the term are derivatives and fractions of such fluids. The number of cells in a sample will generally be at least about $10^3$, usually at least $10^4$ more usually at least about $10^5$. The cells may be dissociated, in the case of solid tissues, or tissue sections may be analyzed. Alternatively a lysate of the cells may be prepared.

For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method depends on the in vitro detection of binding between antibodies and apoE in a lysate. Measuring the concentration of binding in a sample or fraction thereof may be accomplished by a variety of specific assays. A conventional sandwich type assay may be used. For example, a sandwich assay may first attach specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples, of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

A number of assays are known in the art for determining the effect of a drug on animal behavior. Behavioral abnormalities and recovery from acute or chronic injury in animal models are useful for testing the effect, interactions, and specificity of a candidate biologically active agent. Some examples are provided, although it will be understood by one of skill in the art that many other assays may also be used. The subject animals may be used by themselves, or in combination with control animals. Control animals may have the endogenous apoE intact, or may be a combination transgenic, where the normal apoE gene is disrupted, and has been replaced with an exogenous gene, e.g. a human gene, a mutated mouse gene, etc.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

A number of assays are known in the art for determining the effect of a drug on animal behavior and other phenomena associated with neurodegeneration or impairment of cognitive abilities. Some examples are provided, although it will be understood by one of skill in the art that many other assays may also be used. The subject animals may be used by themselves, or in combination with control animals.

The screen using the transgenic animals of the invention can employ any phenomena associated learning impairment, dementia or cognitive disorders that can be readily assessed in an animal model. The screening can include assessment of phenomena including, but not limited to: 1) analysis of molecular markers (e.g. levels of expression of apoE gene products in brain tissue; presence/absence in brain tissue of various apoE isoforms; and formation of neurite plaques); 2) assessment behavioral symptoms associated with memory and learning; 3) detection of neurodegeneration characterized by progressive and irreversible deafferentation of the limbic system, association neocortex, and basal forebrain (neurodegeneration can be measured by, for example, detection of synaptophysin expression in brain tissue)(see, e.g., Games et al. *Nature* 373:523–7 (1995)). These phenomena may be assessed in the screening assays either singly or in any combination.

Preferably, the screen will include control values (e.g., the level of amyloid production in the test animal in the absence of test compound(s)). Test substances which are considered positive, i.e., likely to be beneficial in the treatment of apoE-mediated, will be those which have a substantial effect upon an apoE-associated phenomenon (e.g., test agents that are able to rescue behavioral disorders caused by altered expression of apoE).

Methods of assessing these phenomena, and the effects expected of a candidate agent for treatment of apoE-associated disorders, are known in the art. For example, methods for using transgenic animals in various screening assays for, for example, testing compounds for an effect on AD, are found in WO 9640896, published Dec. 19, 1996; WO 9640895, published Dec. 19, 1996; WO 9511994, published May 4, 1995 (describing methods and compositions for in vivo monitoring of Aβ; each of which is incorporated herein by reference with respect to disclosure of methods and compositions for such screening assays and techniques). Examples of assessment of these phenomena are provided below, but are not meant to be limiting.

PATHOLOGICAL STUDIES

After exposure to the candidate agent, the animals are sacrificed and analyzed by immunohistology for either: 1) neuritic plaques and neurofibrillary tangles (NFTs) in the brain and/or 2) levels of respective isoforms of apoE. The brain tissue is fixed (e.g. in 4% paraformaldehyde) and sectioned; the sections are stained with antibodies reactive with the apoE isoform of interest. Secondary antibodies conjugated with fluorescein, rhodamine, horse radish peroxidase, or alkaline phosphatase are used to detect the primary antibody. These experiments permit identification of amyloid plaques and the regionalization of these plaques to specific areas of the brain.

Sections can also be stained with other diagnostic antibodies recognizing antigens such as Alz-50, tau, A2B5, neurofilaments, neuron-specific enolase, and others that are characteristic of neurodegeneration. Staining with thioflavins and congo red can also be carried out to analyze co-localization of Aβ deposits within the neuritic plaques and NFTs.

ANALYSIS OF apoE EXPRESSION 1) mRNA: mRNA can be isolated by the acid guanidinium thiocyanatephenol:chloroform extraction method (Chomczynski et al., *Anal Biochem* 162:156–159 (1987)) from cell lines and tissues of transgenic animals to determine expression levels by Northern blots.

2) in situ Hybridizations: Radioactive or enzymatically labeled probes can be used to detect mRNA in situ. The probes are degraded approximately to 100 nucleotides in length for better penetration of cells. The procedure of Chou et al. *J Psychiatr Res* 24:27–50 (1990) for fixed and paraffin embedded samples is briefly described below although similar procedures can be employed with samples sectioned as frozen material.

Paraffin slides for in situ hybridization are dewaxed in xylene and rehydrated in a graded series of ethanols and finally rinsed in phosphate buffered saline (PBS). The sections are postfixed in fresh 4% paraformaldehyde. The slides are washed with PBS twice for 5 minutes to remove paraformaldehyde. Then the sections are permeabilized by treatment with a 20 mu g/ml proteinase K solution. The sections are refixed in 4% paraformaldehyde, and basic molecules that could give rise to background probe binding are acetylated in a 0.1M triethanolamine, 0.3M acetic anhydride solution for 10 minutes. The slides are washed in PBS, then dehydrated in a graded series of ethanols and air dried. Sections are hybridized with antisense probe, using sense probe as a control. After appropriate washing, bound radioactive probes are detected by autoradiography or enzymatically labeled probes are detected through reaction with the appropriate chromogenic substrates.

3) Western Blot Analysis: Protein fractions can be isolated from tissue homogenenates and cell lysates and subjected to Western blot analysis as described by Harlow et al., *Antibodies: A laboratory manual*, Cold Spring Harbor, N.Y., (1988); Brown et al., *J. Neurochem* 40:299–308 (1983); and Tate-Ostroff et al., *Proc Natl Acad Sci* 86:745–749 (1989)). Only a brief description is given below.

The protein fractions can be denatured in Laemmli sample buffer and electrophoresed on SDS-polyacrylamide gels. The proteins are be then transferred to nitrocellulose filters by electroblotting. The filters are blocked, incubated with primary antibodies, and finally reacted with enzyme conjugated secondary antibodies. Subsequent incubation with the appropriate chromogenic substrate reveals the position of apoE proteins.

BEHAVIORAL STUDIES OF TRANSGENIC MICE AND RATS

Behavioral tests designed to assess learning and memory deficits can be employed. An example of such as test is the Morris Water maze (Morris *Learn Motivat* 12:239–260 (1981)). In this procedure, the animal is placed in a circular pool filled with water, with an escape platform submerged just below the surface of the water. A visible marker is placed on the platform so that the animal can find it by navigating toward a proximal visual cue. Alternatively, a more complex form of the test in which there are no formal cues to mark the platform's location will be given to the animals. In this form, the animal must learn the platform's location relative to distal visual cues. Alternatively, or in addition, memory and learning deficits can be studies using a 3 runway panel for working memory impairment (attempts to pass through two incorrect panels of the three panel-gates at four choice points) (Ohno et al. *Pharmacol Biochem Behav* 57:257–261 (1997)).

STUDIES OF ANIMAL MODELS OF NEURONAL DAMAGE

Rodent models of neuronal damage, for example neuronal damage caused by cerebral ischemia, may be examined to determine the role of apoE3 and apoE4 in the extent of neuronal damage caused by traumatic events as well as their role in neuronal remodeling, repair and recovery from such insults. Rodent models of cerebral ischemia, both global ischemia and focal ischemia, are useful for studying mechanisms controlling the occurrence of cerebral ischemia and potential therapeutic strategies for treatment of injury caused by ischemic events. Animal models of global ischemia, which is usually transient, have widely affected brain areas but typically give rise to neuronal alternations in selectively vulnerable brain regions. Examples of such models include, but are not limited to, the two vessel occlusion model of forebrain ischemia, the four vessel occlusion model of forebrain ischemia, and ischemia models involving elevated cerebrospinal fluid pressure. See Ginsberg and Busto, *Stroke*, 20:1627–1642 (1989), which is herein incorporated by reference. Models of focal ischemia may mimic ischemic stroke injury, and typically give rise to localized brain infarction. Example of models of focal ischemia include, but are not limited to, middle cerebral artery occlusion, photochemically induced focal cerebral thrombosis, blood clot embolization, microsphere embolization and the like. See McAuley, *Cerebrovasc. Brain Metab. Review*, 7:153–180 (1995) which is herein incorporated by reference.

Any of these models may be used in the transgenic animals of the present invention to examine the role of apoE3 or apoE4, both during traumatic brain injury and in neuronal remodeling and repair following a traumatic ischemic insult to the brain. For example, to examine the role of apoE3 or apoE4 in a rodent stroke model, the rate and nature of injury following cerebral ischemia may be examined using the trangenic animals of the present invention. In such rodent models, the trangenic animals can be subjected to an ischemic injury, and the animals monitored for extent of damage and/or recovery following injury. In addition, the effect of apoE3 and apoE4 may be examined in the neuronal remodeling and recovery of these animal models. The role of the apoE isoforms in these processes may be examined using biochemical, pathological, physiological or behavioral methods, as described in the preceding sections.

Moreover, the effects of different therapies, including the use of therapeutic agents, may be examined to determine potential therapeutic strategies for mitigating and/or reversing the neuronal damage in these animal models. For instance, in a rodent model of focal cerebral ischemia using the animals of the present invention, different candidate therapeutic agents may be administered prior to the induction of the trauma to examine the preventive effect of agents in specific brain regions, and whether that preventive effect in apoE-isoform-dependent. Alternatively, a candidate therapeutic agent may be administered following the induction of the injury to determine the mitigating or recovery effects of that agent, whether the agent is specific to certain brain regions, and if the effect or the specificity of the agent is apoE-isoform dependent.

ADMINISTRATION OF THERAPEUTIC AGENTS

The therapeutic agents may be administered in a variety of ways, orally, topically, parenterally e.g. subcutaneously, intraperitoneally, by viral infection, intravascularly, etc. Inhaled treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carries and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

EXAMPLES

The following examples are put forth so as to provide those of ordinary skill in the art with a complete disclosure and description of how to make and use the subject invention, and are not intended to limit the scope of what is regarded as the invention nor are they intended to represent or imply that the experiments shown are all or the only experiments performed. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

AGE-RELATED NEURODEGENERATION

Animals with an endogenous apoE homozygous knockout were examined as animal models for human age-related neurodegenerative disorders such as AD. To identify specific apoE isoforms involved in the mediation or prevention of age-related neurodegeneration, apoE knockout (Apoe$^{-/-}$) mice were transformed with transgenes encoding either human apoE3 or apoE4 under the control of the neuron-specific enolase (NSE) promoter (FIG. 1). These transgenic mice were examined for progression of age-related neurodegeneration and promotion of neuronal repair/remodeling. Aged Apoe$^{-/-}$ mice, which exhibit significant loss of presynaptic terminals and neuronal dendrites in the neocortex and hippocampus, were used as a negative control in the study.

GENERATION OF TRANSGENIC MICE

The rat neuron-specific enolase (NSE) promoter directs panneuronal expression of fusion gene constructs in the CNS of transgenic mice (Forss-Petter et al., Neuron, 5:187–197 (1990)). These NSE-apoE3 and NSE-apoE4 transgenes (FIG. 1) were used to generate apoE knockout (Apoe$^{-/-}$) mice expressing apoE3 or apoE4 in the brain. Transgenic founder mice (9 NSE-apoE3 and 12 NSE-apoE4) were identified by Southern blot analysis. One NSE-apoE3 line and one NSE-apoE4 line derived from these founders that showed similar levels of human apoE expression were selected for further study.

Four subgroups of mice were studies: wild-type mice, Apoe$^{-/-}$ mice, and Apoe$^{-/-}$ mice heterozygous for the NSE-apoE3 transgene (NSE-apoE3 mice) or the NSE-apoE4 transgene (NSE-apoE4 mice). NSE-apoE transgenic mice on the Apoe$^{-/-}$ background were generated as follows. NSE-apoE transgenes were injected individually into one-cell ICR embryos by standard procedures; transgenic lines were established from transgenic founders. NSE-apoE3 and NSE-apoE4 lines with matching cerebral levels of transgene expression were selected and crossed with Apoe$^{-/-}$ mice (Piedrahita et al., 1992) provided by Dr. Nobuyo Maeda (University of North Carolina, Chapel Hill). After elimination of wild-type ApoE alleles in two generations of breedings among the resulting offspring, transgenic mice were crossed with Apoe$^{-/-}$ mice [C57BL/6J-Apoe$^{tm1Unc}$] from Jackson Laboratories (Bar Harbor, Me.) to generate the cohorts of NSEapoE3 and NSE-apoE4 mice used in this study. The same crosses also yielded nontransgenic Apoe$^{-/-}$ littermates (n=9). Comparison of the latter mice with age-matched C57BL/6J-Apoe$^{tm1Unc}$ from Jackson Laboratories (n=13) revealed no significant differences in any of the variables examined (data not shown). Therefore, these two cohorts of mice were combined (Apoe$^{-/-}$ mice) in our statistical analyses. Each of these subgroups (n=3–12) were analyzed for two different age ranges, 3–4 months, and 7–9 months.

SCREENING OF TRANSGENIC ANIMALS

To identify mice transgenic for NSE-apoE3 or NSE-apoE4, genomic tail DNA was analyzed by Southern blot analysis with a DNA probe for human APOE (Ballota et al., J. Clin. Invest. 96:2170–2179 (1995)). NSE-apoE3 and NSE-apoE4 mice were differentiated by polymerase chain reaction (PCR). Because human APOE intron 3 was included in the NSE-apoE4 but not in the NSE-apoE3 construct, the amplicon generated with intron 3-spanning primers (forward primer: nucleotides 3158–3175; reverse primer: nucleotides 3815–3834, GenBank accession number M10065) was 670 base pairs (bp) in NSE-apoE4 mice and 100 bp in NSE-apoE3 mice. Proteinase K-digested tail tissue (1:100 dilution, 2 µl) was subjected to touchdown PCR (Hecker and Roux, 1996) in a total reaction volume of 25 µl with each primer (0.2 µM), dNTP's (dATP, dCTP, dGTP, dTTP, 200 µM each), and 0.15 µl of AmpliTaq GoldR DNA polymerase (Perkin Elmer, Norwalk, Conn.). The reaction was run on a GeneArnp PCR System 9600 (Perkin Elmer) thermocycler. PCR products were analyzed on 1.5% agarose gels.

TISSUE PREPARATION

Mice were anesthetized with chloral hydrate or metoxyflurane and flush-perfused transcardially with 0.9% saline. Tissues were immediately dissected, snap-frozen, and stored at −70° C. until extraction of protein or RNA. Brains were removed and divided sagitally. One hemibrain was postfixed in phosphate-buffered 4% paraformaldehyde (pH 7.4) at 4° C. for 48 hr for vibratome sectioning; the other was snap frozen and stored at −70° C. for RNA or protein analysis. Normal human brain (occipital lobe) was obtained from Dr. Tom M. Hyde, National Institute of Mental Health, Bethesda, Md. AD brain was obtained from Dr. Eliezer Masliah (University of California, San Diego).

TISSUE-SPECIFIC DISTRIBUTION OF APOE3 AND APOE4

Human apoE expression in NSE-apoE3 and NSE-apoE4 mice, determined by RNase protection assay (RPA), was found primarily in neural tissues and gonads. Immunoblotting showed no human apoE in the plasma of NSE-apoE mice. Plasma lipoprotein cholesterol levels in the NSE-apoE mice were similar to those in nontransgenic Apoe$^{-/-}$ littermate controls).

RNA EXTRACTION AND ANALYSIS

Total RNA was isolated from tissues with TRI-Reagent (Molecular Research Center, Cincinnati, Ohio) or Tripure (Boehringer Mannheim, Indianapolis, Ind.). RNA was analyzed by solution hybridization RPA with antisense riboprobes complementary to human apoE mRNA [nucleotides 281–469 of APOE cDNA (GenBank accession number M12529)] or β-actin mRNA [nucleotides 480–559 of mouse β-actin cDNA (GenBank accession number M18194)]. Because the apoE riboprobe also protects a smaller fragment of endogenous mouse apoE mRNA sequence, human and mouse apoE mRNAs could be differentiated. RPAs were carried out essentially as described (Bordonaro et al., Bio Techniques, 16:428–430 (1994)). Briefly, sample RNA (10 µg) hybridized to $^{32}$P-labeled antisense riboprobes were digested with 300 U/ml RNase T1 (GIBCO, Gaithersburg, Md.) and 0.5 µg/ml RNase A (Sigma, St. Louis, Mo.) in 100 µl of digestion buffer, followed by protein digestion with 10 mg/ml proteinase K (Sigma). RNA was isolated-with 4 M guanidine thiocyanate and precipitated in isopropanol. Samples were separated on 5–6% acrylamide/8 M urea TBE gels, and the dried gels were exposed to XAR or Biomax MS film (Kodak, Rochester, N.Y.). Levels of specific transcripts were estimated by quantitating probe-specific signals with a phosphorimager (FUJI-BasIII, Fuji Photo Film Co., Tokyo, Japan); β-actin signals were used to correct for differences in RNA content/loading (Johnson et al., Glia, 13:174–184 (1995)).

ANALYSIS OF CSF

After metoxyflurane overdose and exsanguination by cardiac puncture, CSF was obtained from nine NSE-apoE3, nine NSE-apoE4, and eight Apoe$^{-/-}$ mice. We modified the procedure described by Carp et al. (1971) by using a 25-gauge needle attached to silicon tubing (0.012" i.d.) and piercing the dura mater tangentially. Slight negative pressure was exerted with a tuberculin syringe to start the flow. About 10 µl of CSF was obtained per adult mouse from the cisterna magna with little or no contaminating blood. The CSF was centrifuged in a desktop centrifuge to remove contaminating cells, at 4° C., and used within 3 days for western blotting and quantitation of apoE. Equal volumes of CSF from the mice were applied to the gels.

WESTERN BLOT ANALYSIS

Brain homogenates were prepared from hemibrains with a triple detergent lysis buffer (Sambrook et al., Molecular Cloning: A Laboratory Manual (1989)) and protease inhibitors (phenylmethylsulfonyl fluoride [100 µg/ml], aprotinin [1 µg/ml], and complete inhibitor [2×, catalog no. 1836145, Boehringer Mannheim]). Insoluble material was removed by centrifugation. The protein concentration in the supernatant was determined with a modified Bradford method (Pierce), and sample protein concentrations were equalized with lysis buffer. Sodium dodecyl sulfate loading buffer was added, and the samples were heated to 95° C. for 5 minutes. To quantiate apoE in brain tissue and CSF, samples and purified apoE standards were separated by sodium dodecyl sulfate-polyacrylamide gel electrophoresis, electrotransferred to nitrocellulose membranes (Bio-Rad, Hercules, Calif.), and blocked with phosphate-buffered saline (PBS) containing 5% dried milk and 0.05% Tween. The blots were incubated in polyclonal goat anti-human apoE antibody (1:1000, Calbiochem, San Diego, Calif.) or in polyclonal rabbit anti-mouse apoE antibody (1:1000). The bound primary antibodies were detected by horseradish peroxidase-conjugated species-specific antibodies (Amersham, Arlington, Ill.). Immunodetection was carried out according to the manufacturer's instructions using SuperSignal Ultra (Pierce) or ECL (Amersham), and the blots were exposed to X-ray film (Biomax MR, Kodak). For semiquantitative assessments of apoE, known quantities of purified human plasma apoE3 or apoE4 (prepared as described by Rall et al., 1986) or recombinant mouse apoE were run as standards on the same gels. For quantitation, exposures of western blots with densities within the linear range of the film were scanned (Powerlook II, Umax), and the density of the bands was determined by inflection point analysis with Advanced Quantifier software (Bio Image, Ann Arbor, Mich.).

APOE MRNA AND PROTEIN LEVELS IN THE BRAIN AND CSF

Figure 2:
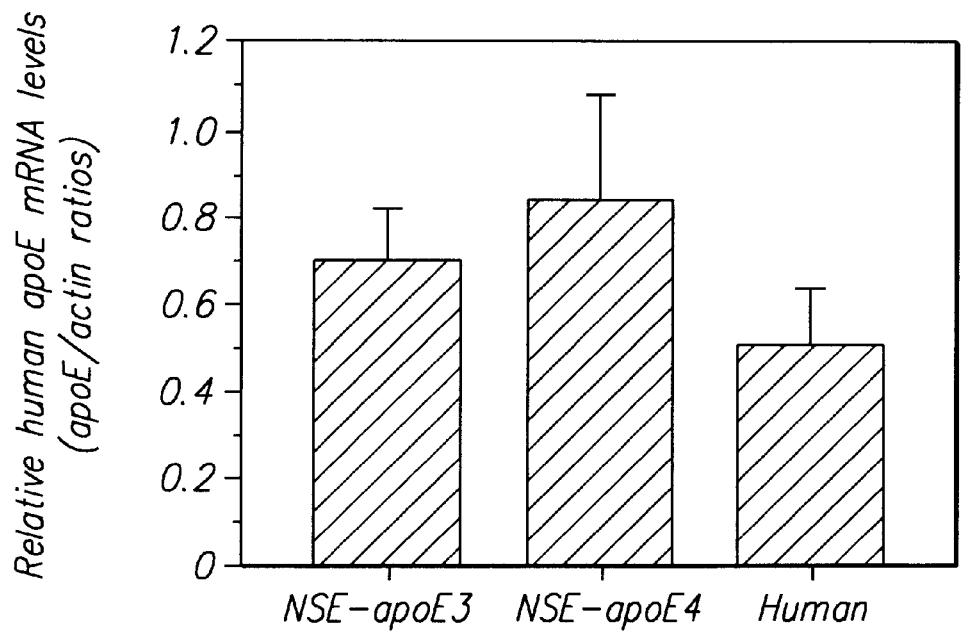
FIG. 2 is a bar graph showing a semiquantitative comparison of human apoE mRNA levels in the brain tissue of NSE-apoE mice and humans.
Figure 3:
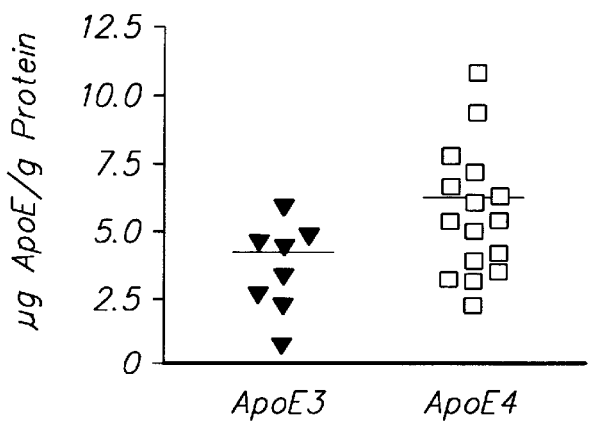
FIG. 3 is a graph illustrating the apoE content of brains of human apoE3 and apoE4 transgenic mice as determined by densitometric standards. Each inverted triangle represents levels in a single NSE-apoE3 transgenic mouse, and each open square represents the levels in a single NSE-apoE4 transgenic mouse.

RPA demonstrated similar steady-state levels of human apoE mRNA in the brains of NSE-apoE3 and NSE-apoE4 mice (FIG. 2). Similar levels were found in human frontal cortex. Human apoE protein levels, assessed by Western blot analysis, were similar in human and transgenic mouse brains. No apoE was detected in ApoE$^{-/-}$ mice. Densitometric scanning of gels also showed similar apoE levels in NSE-apoE3 and NSE-apoE4 mice (FIG. 3). Both mouse and human brain apoE possessed two major bands in the 34–38 kD range. Consistent with previously reported results, CNS apoE appeared to be highly sialylated, accounting for a higher molecular weight band compared to purified plasma apoE standard. The human apoE and apoE4 in the transgenic mouse brains was intact, and no significant degradation products were found. Western blot analysis demonstrated similar levels of human apoE in CSF from NSE-apoE3 and NSE-apoE4 mice. No apoE was detected in the CSF of ApoE$^{-/-}$ mice.

IMMUNOHISTOCHEMISTRY

Postfixed tissues were cut into 40-μm-thick sections with a vibratome and incubated in 0.3% $H_2O_2$ in PBS for 20 minutes to quench endogenous peroxidase activity. To facilitate penetration of antibodies, sections used for immunoperoxidase staining were preincubated for 4 minutes in 1 μg/ml proteinase K in a buffer containing 250 mM NaCl, 25 mM EDTA, 50 mM Tris/HCl, pH 8. All sections were blocked for 1 hr with 15% normal donkey serum (Jackson ImmunoResearch, West Grove, Pa.) in PBS or for 7 minutes in Superblock (Scytec, Logan, Utah). Blocking was followed by a 1-hr incubation in PBS with the primary antibody, polyclonal goat anti-human apoE (Calbiochem) diluted 1:4,000 (immunofluorescent staining) or 1:10,000 (immunoperoxidase staining) to detect human apoE. Polyclonal rabbit anti-rat apoE diluted 1:1000 (gift from Dr. Karl Weisgraber) was used to detect murine apoE. Sections were then washed twice in PBS and incubated for 1 hr with the secondary antibody: FITC-(Jackson ImmunoResearch) or biotin-labeled (Vector, Burlingame, Calif.) anti-goat to detect antigen-bound anti-human apoE or FITC-labeled anti-rabbit (Vector) to detect antigen-bound anti-rat apoE. After three washed in PBS, immunofluorescently labeled sections were mounted in VectraShield (Vector) and viewed with a MRC-1024 laser scanning confocal microscope (Bio-Rad) mounted on an Optiphot-2 microscope (Nikon, Tokyo, Japan). For immunoperoxidase staining, secondary antibody binding was detected with the ABC-Elite kit (Vector).

The intensity of human apoE immunolabeling of neurons in brains of NSE-apoE mice was determined on immunofluorescently labeled sections with the MRC-1024 using the Lasersharp software. A 10 μm line was drawn through the cytoplasm of five randomly selected neocortical neurons per animal, and intensity of the pixels across this line was determined, and the mean pixel intensity per line Nvas calculated.

Double-labeling for human apoE and MAP-2 was performed as described above except that sections were incubated with anti-MAP-2 antibody (1:40, Boehringer Mannheim) together with anti-human apoE. To detect primary antibody binding, sections were incubated for 1 hr in a mixture of secondary antibodies (Jackson ImmunoResearch), each diluted 1:100: α FITC-conjugated donkey anti-goat (to detect anti-human apoE) and a Cy5-conjugated donkey anti-mouse (to detect anti-MAP-2). After three 10-minute washes in PBS, sections were mounted under glass coverslips with VectaShield (Vector) and viewed by confocal microscopy as described above. The Cy5 and FITC channels were viewed individually, and the resulting images were pseudocolored in red (Cy5) or green (FITC) with Adobe Photoshop. Omission of primary antibodies or incubation of sections with mismatched primary and secondary antibodies resulted in no labeling. To exclude the possibility that the signals collected in the FITC channel originated from emission light from the Cy5 fluorophore and vice versa, sections labeled with anti-human apoE and FITC-conjugated secondary antibody were imaged in the Cy5 channel, and sections labeled with anti-MAP-2 and Cy5 conjugated secondary antibody were imaged in the FITC channel. No signals were detected under these conditions.

Antibodies against human apoE3 and apoE4 were used to map human apoE expression in immunolabeled brain sections from NSE-apoE3 and NSE-apoE4 mice. Brains from both groups showed similar widespread neuronal expression of human apoE, most prominently in the neocortex and hippocampus.

Confocal microscopic analysis of immunolabeled brain sections from NSE-apoE mice and from a human AD case revealed a similar intraneuronal distribution of apoE3 and apoE4 in the transgenic mice and confirmed the presence of human apoE in astrocytes and neurons in the AD brain. In transgenic brains, apoE3 and apoE4 were identified in a patchy distribution throughout most of the neuronal soma with clear sparing of the nucleus. Little human apoE was detected in neuronal axons or dendrites and none in non-neuronal cells. In the human AD case, intraneuronal apoE immunoreactivity was more diffuse and extended into neuronal processes. Double-labeling with antibodies against human apoE and the neuronal marker microtubule-associated protein 2 (MAP-2) confirmed the neuronal identify of the brain cells expressing human apoE in NSE-apoE3 and NSE-apoE4 mice.

Comparison of the neuronal human apoE immunofluorescence signals in 3–4 and 7–9 month-old NSE-apoE3 and NSE-apoE4 mice (n=4–5/group) showed no significant differences in immunostaining intensity. These results are consistent with those obtained by RPA and Western blot analysis.

SEMIQUANTITATIVE ASSESSMENT OF NEURONAL INTEGRITY

Immunolabeling of brain sections for MAP-2 (a marker of neuronal cell bodies and dendrites) and for synaptophysin (a marker of presynaptic terminals), analysis of labeled sections with a Bio-Rad MRC-1024 mounted on a Nikon Optiphot-2 microscope, and computer-aided semiquantitative analysis of confocal images were carried out essentially as described (Masliah et al., Exp. Neurol. 136:107–122 (1992); Toggas et al., Nature 367:188–193 (1994)). Neuronal integrity was assessed in the neocortex and in the pyramidal cell layer of the hippocampus in four sections per animal (two for each marker). Binding of primary antibodies (Boehringer Mannheim) was detected with a FITC-labeled secondary antibody (Vector). Sections were assigned code numbers to ensure objective assessment, and codes were not broken until the analysis was complete. For each mouse, we obtained 4–8 confocal images (3–4/section) of the neocortex and 2–4 confocal images (1–2/section) of the hippocampus, each covering an area of 210×140 gm. Digitized images were transferred to a PowerMacintosh computer and analyzed with Image 1.5. The area of the neuropil occupied by MAP-2-immunolabeled dendrites or by synaptophysin-immunolabeled terminals was quantified and expressed as a percentage of the total image area as described (Masliah et al., id.).

Figure 4:
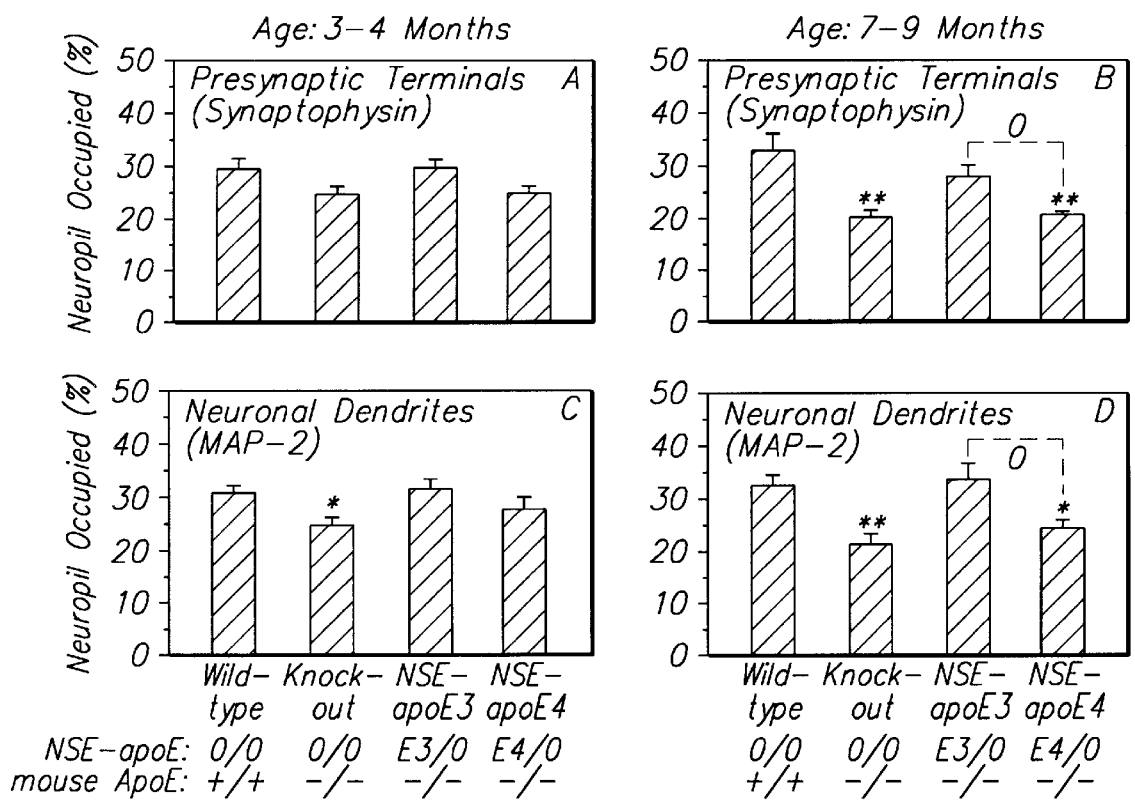
FIGS. 4(A–D) is a series of graphs labeled A, B, C and D illustrating the neuronal expression of human ApoE in NSE-apo3 and NSE-apo4 transgenic mouse brains.

Neuronal integrity in control mice and ApoE$^{-/-}$ mice at both 3–4 and 7–9 months of age was determined to confirm age-related neurodegeneration. Presynaptic terminals and neuronal dendrites were identified with antibodies against synaptophysin and MAP-2, respectively. Immunolabeled sections of neocortex and hippocampus were imaged by confocal microscopy, and the percent area of neurophil occupied by presynaptic terminals or neuronal dendrites was determined by computer-aided analysis of the confocal images. Compared with age-matched wild-type controls, ApoE$^{-/-}$ mice showed significant loss of presynaptic terminals and neuronal dendrites in the neocortex and hippocampus as they aged (FIG. 4).

In NSE-apoE3 and NSE-apoE4 mice, apoE3 prevented the age-dependent degeneration of pre-synaptic terminals and neuronal dendrites found in ApoE$^{-/-}$ mice, whereas apoE4 did not. For both measures of neuronal integrity examined, NSE-apoE3 mice closely resembled wild-type mice. In contrast, NSE-apoE4 mice, like ApoE$^{-/-}$ mice, had significant loss of presynaptic terminals and neuronal dendrites at 7–9 months of age. The development of neurodegenerative chanes in NSE-apoE4 mice was clearly age-dependent, since significant deficits were only seen in the older mice.

STATISTICAL ANALYSES

All results are expressed as mean ±SEM. Differences between means were assess by unpaired two-tailed t test. Differences among means were evaluated by one-way analysis of variance followed by Dunnett's or Tukey-Kramer posthoc test. The null hypothesis was rejected at the 0.05 level.

Example 2

GENDER-DEPENDENT BEHAVIOR IMPAIRMENTS

Animals with an endogenous apoE homozygous knockout were examined as animal models for human spatial learning and memory impairment. To identify specific apoE isoforms involved in the mediation or prevention of age-related behavior impairment, apoE knockout (Apoe$^{-/-}$) mice were transformed with transgenes encoding either human apoE3 or apoE4 under the control of the neuron-specific enolase (NSE) promoter (FIG. 1). Transgenic mice were generated as in Example 1. Four subgroups of mice were studied: wild-type mice, Apoe$^{-/-}$ mice, and Apoe$^{-/-}$ mice heterozygous for the NSE-apoE3 transgene (NSE-apoE3 mice) or the NSE-apoE4 transgene (NSE-apoE4 mice). Males and females of each group were tested independently for behavior impairment and other markers of potential cognitive dysfunction.

Male ApoE$^{-/-}$ mice show structural alterations including diminished regenerative capacity after hippocampal lesioning at 6, but not at 3 months of age, and learning deficits at 6 months of age. Therefore, spatial learning and memory of both 3 and 6 month-old mice was assessed by a water maze test, in which the ability of mice to locate a hidden submerged platform in a pool was tested in two blocks (2-hour interval) of two trials each per day for 4 days.

To minimize the effects of social influences on behavior, all mice were housed singly under conditions of constant temperature (18° C.), light from 6:00 a.m. to 6:00 p.m., and access to food and water. The heterozygous transgenic mice and nontransgenic ApoE$^{-/-}$ littermate controls were crossed for five generations with ApoE$^{-/-}$ mice [Piedrahita, 1992 #78951] that were backcrossed on the C57BL/6J background for six generations. They were subsequently backcrossed on the C57BL/6J background for two generations and contain about 74% C57BL/6J.

GENOTYPING

Tail biopsies were obtained from the mice. Polymerase chain reaction (PCR) or slot blot analysis was used for genotyping. For the slot blot analysis, the insert of the NSE-apoE3 or NSE-apoE4 plasmid was used as template to distinguish ApoE transgenic mice from ApoE$^{-/-}$ littermate controls.

Figure 5:
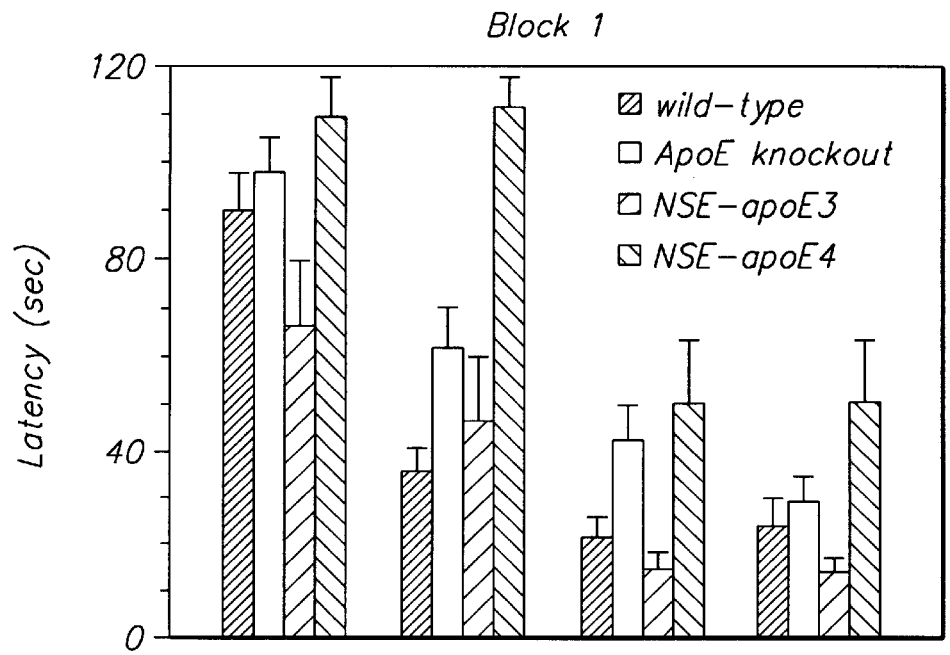
FIG. 5 is a bar graph showing the mean time to locate the hidden platform (latency) of 6 month-old male mice in block 1 of the water maze test.
Figure 6:
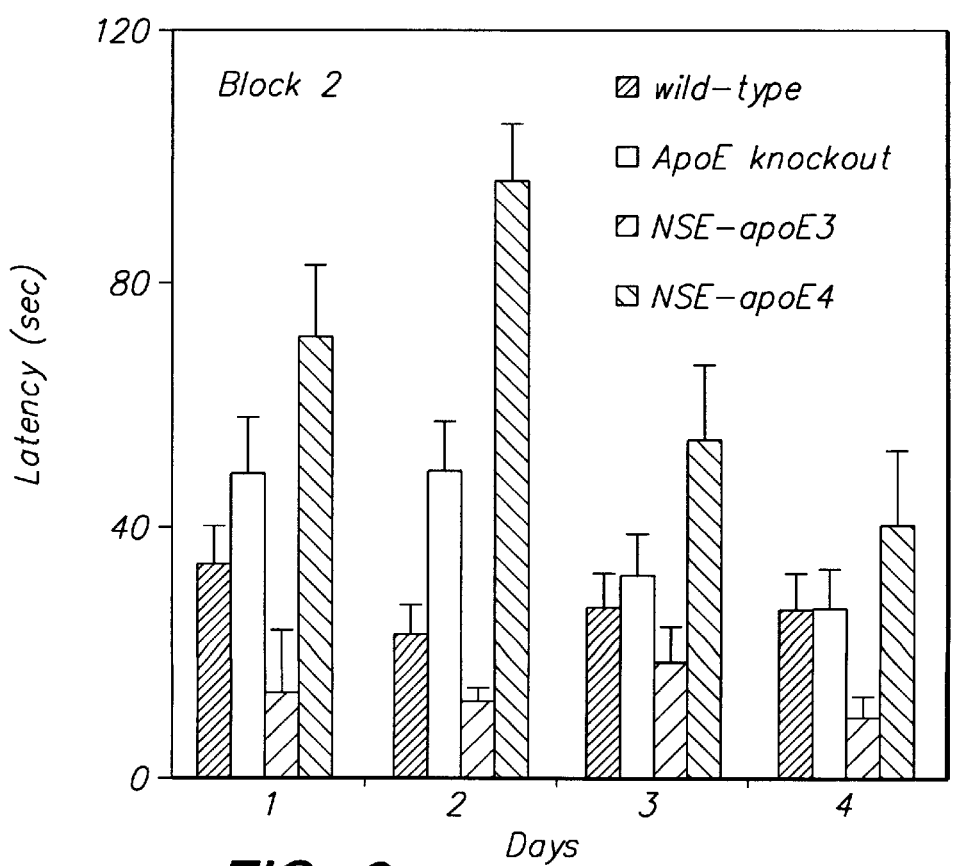
FIG. 6 is a bar graph showing the mean time to locate the hidden platform (latency) of 6 month-old male mice in block 2 of the water maze test.

In the 6-month-old female groups, all groups improved their performance over 4 days, but their learning curves were markedly different. The wild-type mice performed significantly better than the ApoE$^{-/-}$ mice in both blocks of trails (FIGS. 5 and 6). Neuronal expression of apoE3 not only rescued the impaired performance of the ApoE knockout mice, but NSE-apoE3 mice also performed significantly better than wild-type mice in both blocks of trials. In contrast, the NSE-apoE4 mice performed significantly worse than ApoE knockout mice. Similar differences between the groups were observed in path length. On day 5, the mice were tested to locate a clearly visible platform to exclude differences in vision, swimming speed, and motivation. The average swimming speeds of the four groups were similar, and the mice that performed worse than the wild-type mice in locating the hidden platform did not show any impairment in locating the visible platform.

Figure 7:
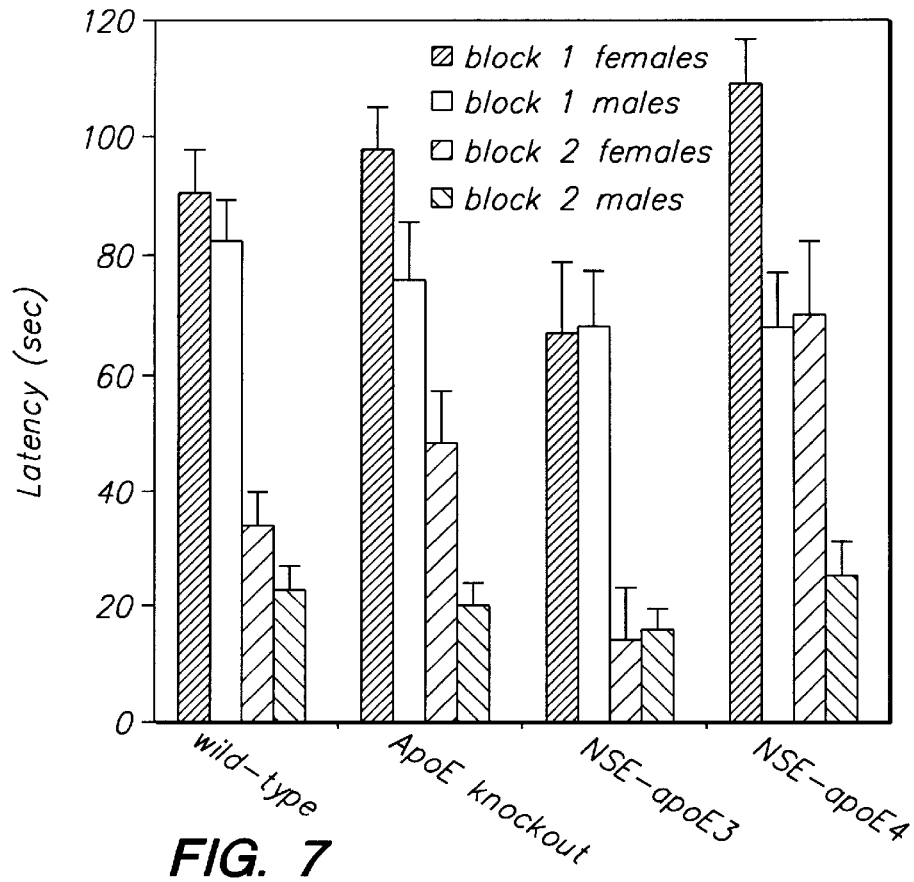
FIG. 7 is a bra graph illustrating gender differences in time needed to locate the hidden platform (latency) in the first and second block of the water maze test (n=6–22 mice per group).

In contrast to the 6-month-old female groups, the 6-month-old male groups showed no significant differences in the learning curves. The NSE-apoE3 males performed slightly better than the other three groups, but the differences were not statistically significant. The gender differences in spatial learning in the water maze are illustrated in FIG. 7, which shows the times to locate the hidden platform on the first day. The average swimming speeds of male and female mice were similar. Gender had a highly significant effect on time to locate the hidden platform (p<0.01). In the wild-type, Apoe knockout, and NSE-apoE4 mice, the males performed better than the females. Interestingly, the gender difference in NSE-apoE4 mice was larger than the one in Apoe knockout mice, and the gender differences in both groups were larger than the old in wild-type mice. These data indicate that female mice are more susceptible to spatial learning impairments in the water maze. Strikingly, in the NSE-apoE3 mice, which performed even better than the wild-type mice, there is not longer a gender difference in water maze learning.

The normal learning we found in the 6 month-old ApoE$^{-/-}$ males is in contrast to the small or severe learning impairments previously reported in such mice (Gordon et al., Neurosci. Let. 199-1-4 (1995); Oitzl et al., Brain Research, 752: 189–196 (1997)). Strain differences and the use of different water maze designs may have contributed to the differences. We chose C57BL/6 as background strain because they are good learners in both the water maze and in contextual fear-conditioning tasks.

Figure 8:
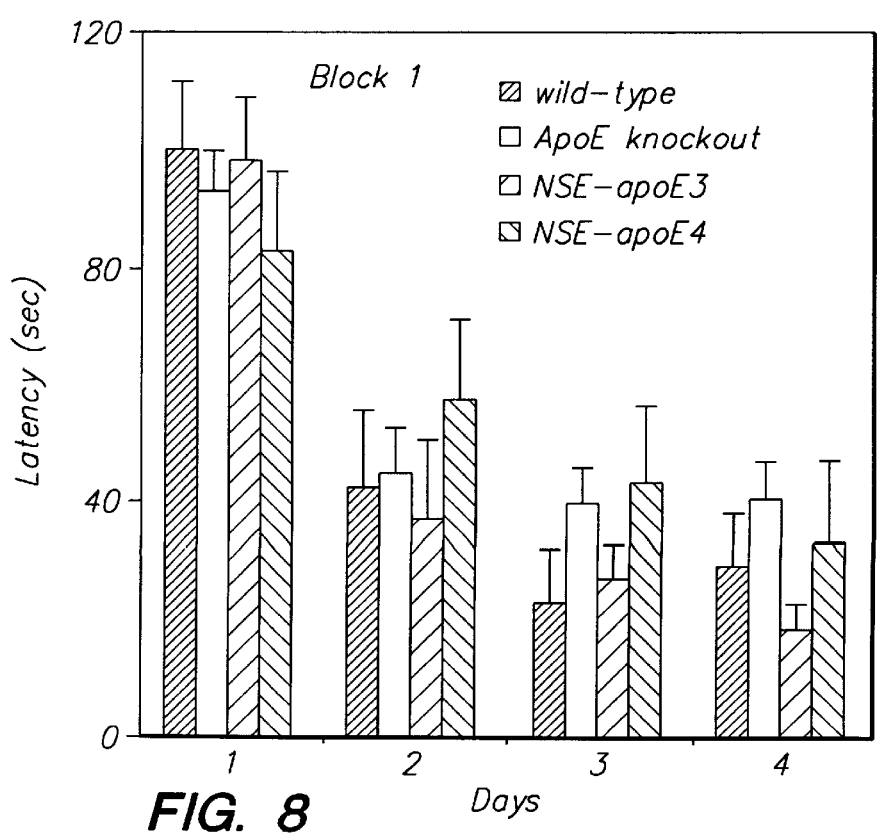
FIG. 8 is a bar graph showing the mean time to locate the hidden platform (latency) of 6 month-old female mice in block 1 of the water maze test.
Figure 9:
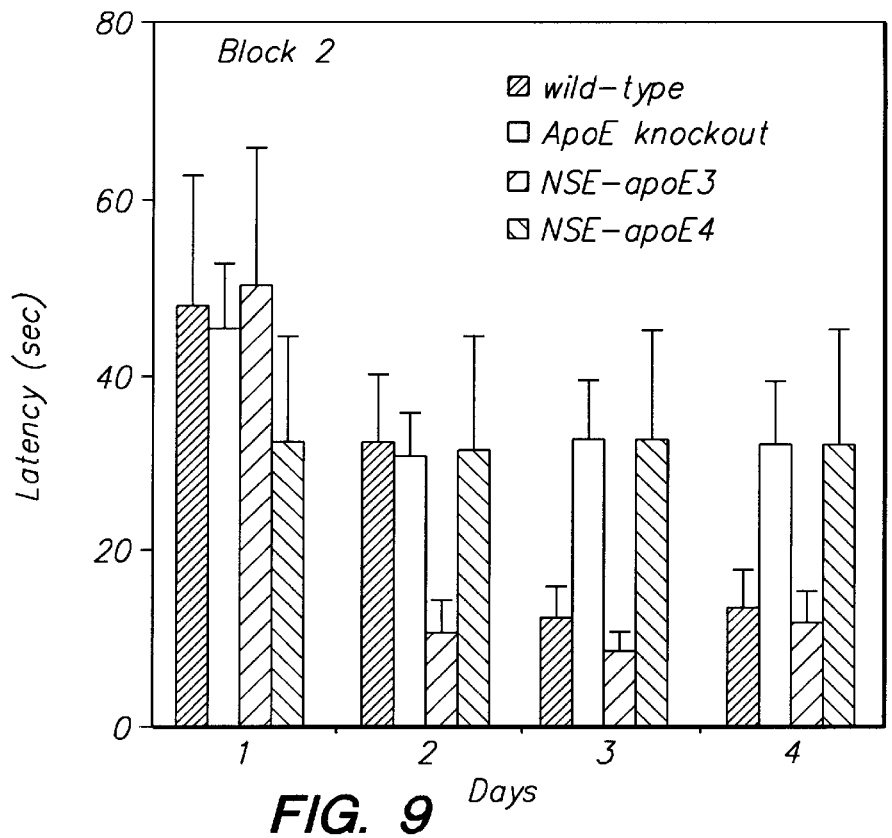
FIG. 9 is a bar graph showing the mean time to locate the hidden platform (latency) of 6 month-old female mice in block 2 of the water maze test.

Spatial learning and memory was assessed in 3-month-old female mice to determine if the behavioral impairments precede the structural alterations that are not observed at this point. In block 1, NSE-apoE3 performed slightly better than the three other groups but there were no large differences between the groups (FIG. 8). However, in block 2, the wild-type and NSE-apoE3 mice performed significantly better than Apoe knockout and NSE-apoE4 mice (FIG. 9). In contrast to the 6 month-old females, there was no difference between ApoE$^{-/-}$ and NSE-apoE4 mice. The average swimming speeds of the four groups were similar, and the mice showed similar performance in locating the visible platform. These results indicate that the behavioral impairments precede the structural alterations and worsen with the onset of these alterations, and that after challenge having apoE4 is worse than having no Apoe at all.

OPEN FIELD ACTIVITY

Open field activity was assessed to determine possible differences in overall activity levels. To quantitate open field activity, mice were placed in brightly lit, individual automated infrared photocell activity cages interfaced with a computer (San Diego Instruments). The data were converted and the following parameters calculated per interval: active time (defined as time, to within 1 second, in which a new beam is broken), distance moved, and rearing times and events. The open field activity was recorded for three consecutive 10-minute intervals after a 1 minute adaptation period. Before and after assessments of open field activity, passive avoidance learning, and rotorod performance, the equipment was cleaned with 1 mM acetic acid to remove residual odors.

Figure 10:
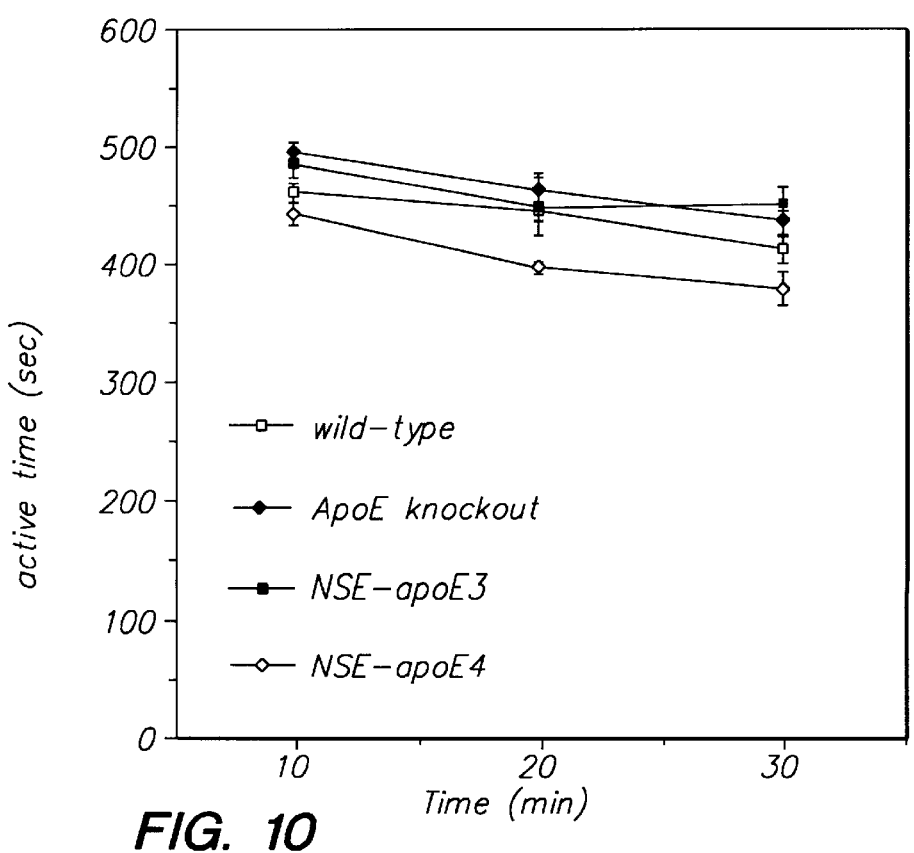
FIG. 10 is a graph showing active times of 6 month-old female mice during open field activity.
Figure 11:
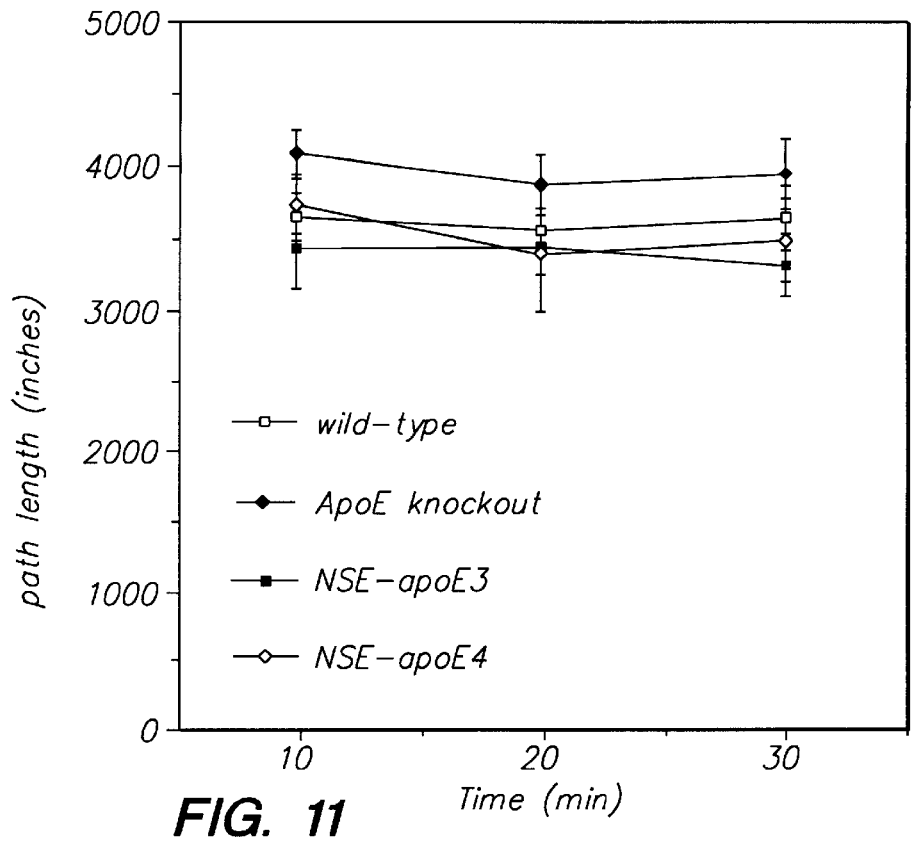
FIG. 11 is a graph showing path length of 6 month-old female mice during open field activity.
Figure 12:
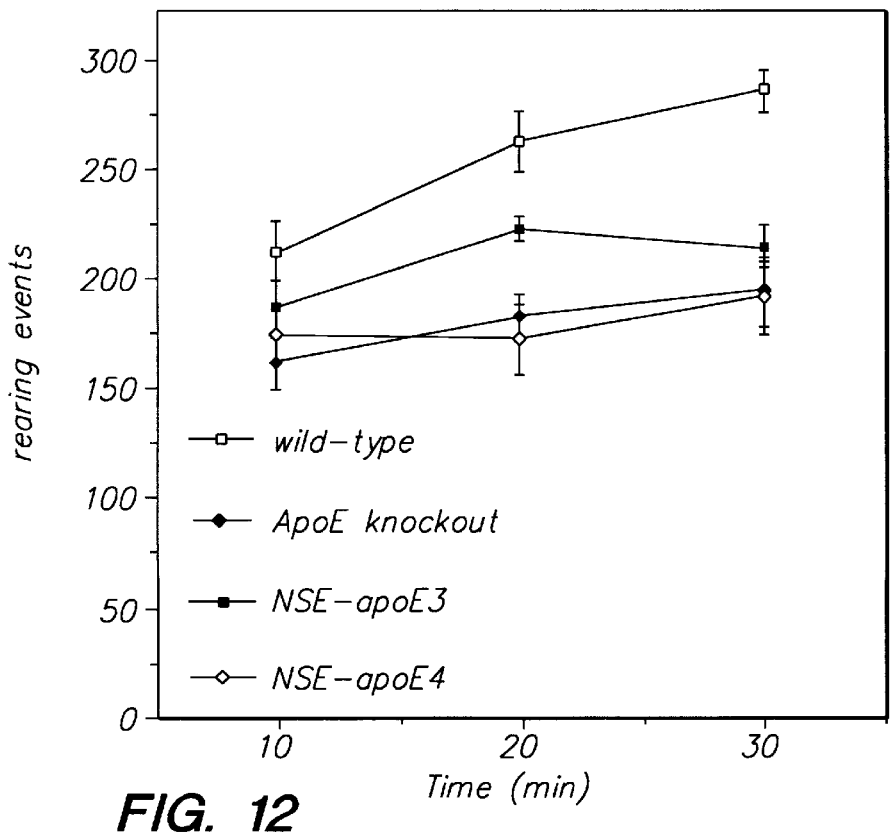
FIG. 12 is a graph showing rearing events of 6 month-old female mice during open field activity.
Figure 13:
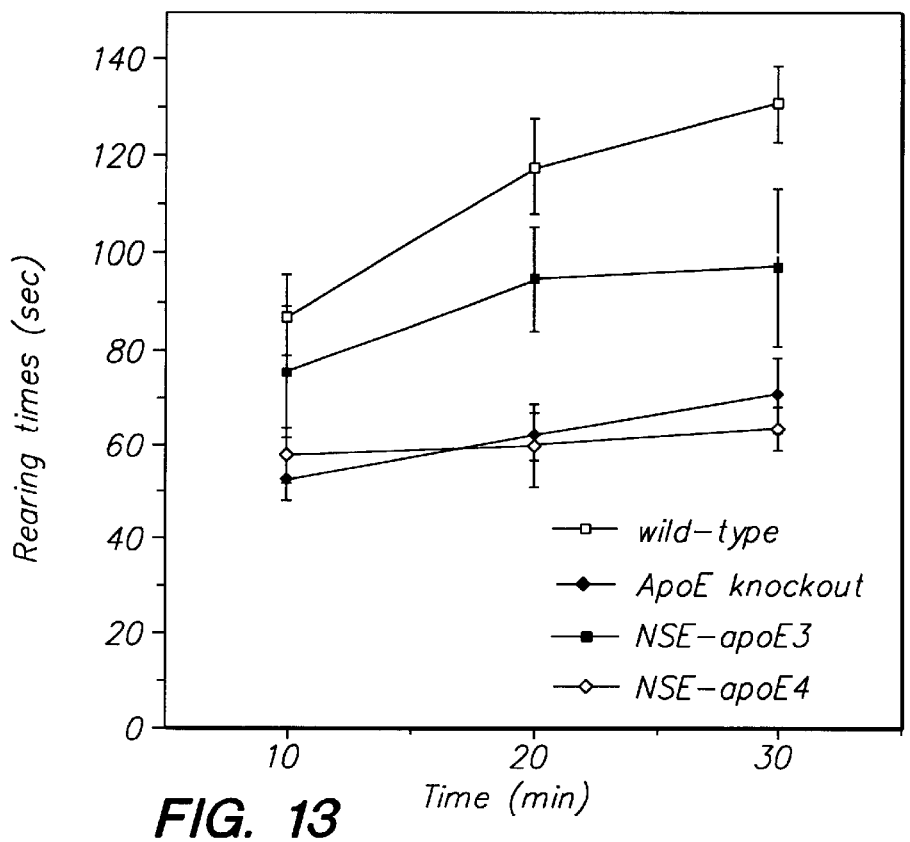
FIG. 13 is a graph showing rearing times of 6 month-old female mice during open field activity.

Active times and path length were very similar in the different 6-month-old female groups (FIGS. 10 and 11), indicating that differences in overall activity do not contribute to the spatial learning impairments observed in the water maze. Rearing (raising both forefeet off the group and extending the body) is a measure of exploratory activity. Strikingly, both the frequency and duration of rearing events differed between the 6 month-old female groups (FIGS. 12 and 13). Both measurements were significantly and similarly reduced in Apo3 knockout and in NSE-apoE4 mice compared with wild-type controls. However, these reductions were partially rescued in the NSE-apoE3 mice.

PASSIVE AVOIDANCE LEARNING

Passive avoidance learning was measured with a step-through box (San Diego Instruments) consisting of a brightly lit compartment and a dark compartment connected with a sliding door. A mouse was placed in the lighted compartment. When the mouse entered the dark compartment, the sliding door was closed, and the mouse received a slight foot shock (0.3 mA, 1 second). Twenty-four hours later, the mouse was again placed into the lighted compartment and latency to enter the dark compartment was recorded up to 300 seconds (criterion).

Figure 14:
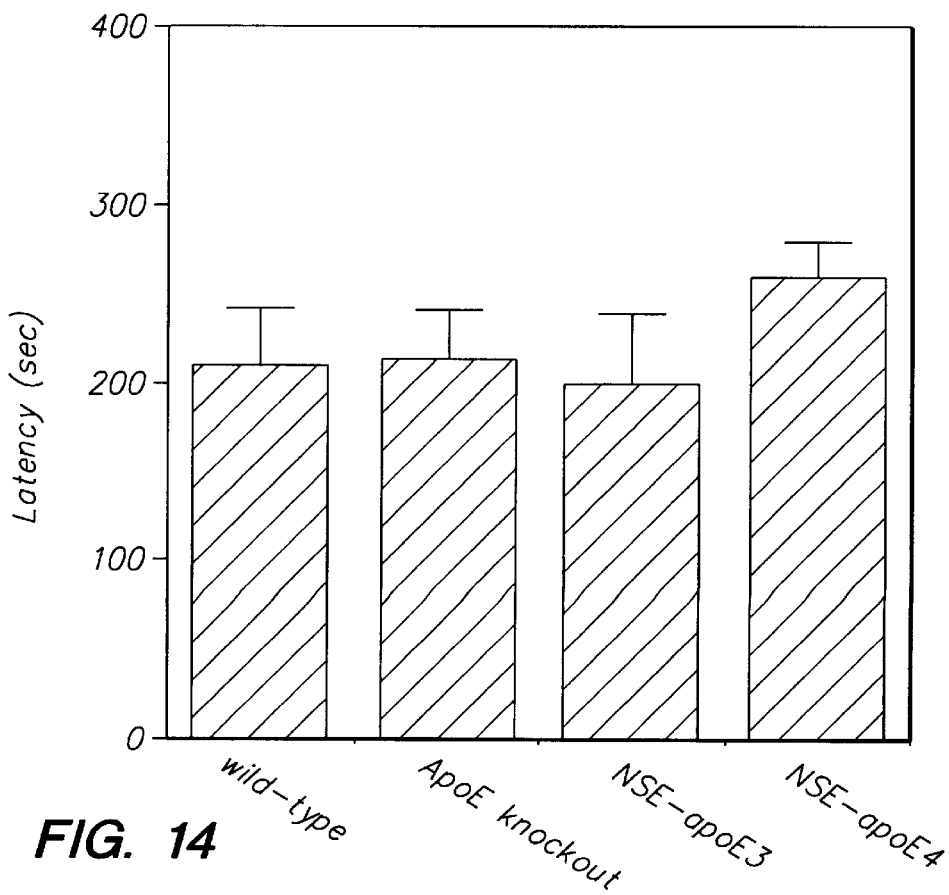
FIG. 14 is a bar graph illustrating time required of the female transgenic mice to reenter a dark compartment following a foot shock 24 hours previously.
Figure 15:
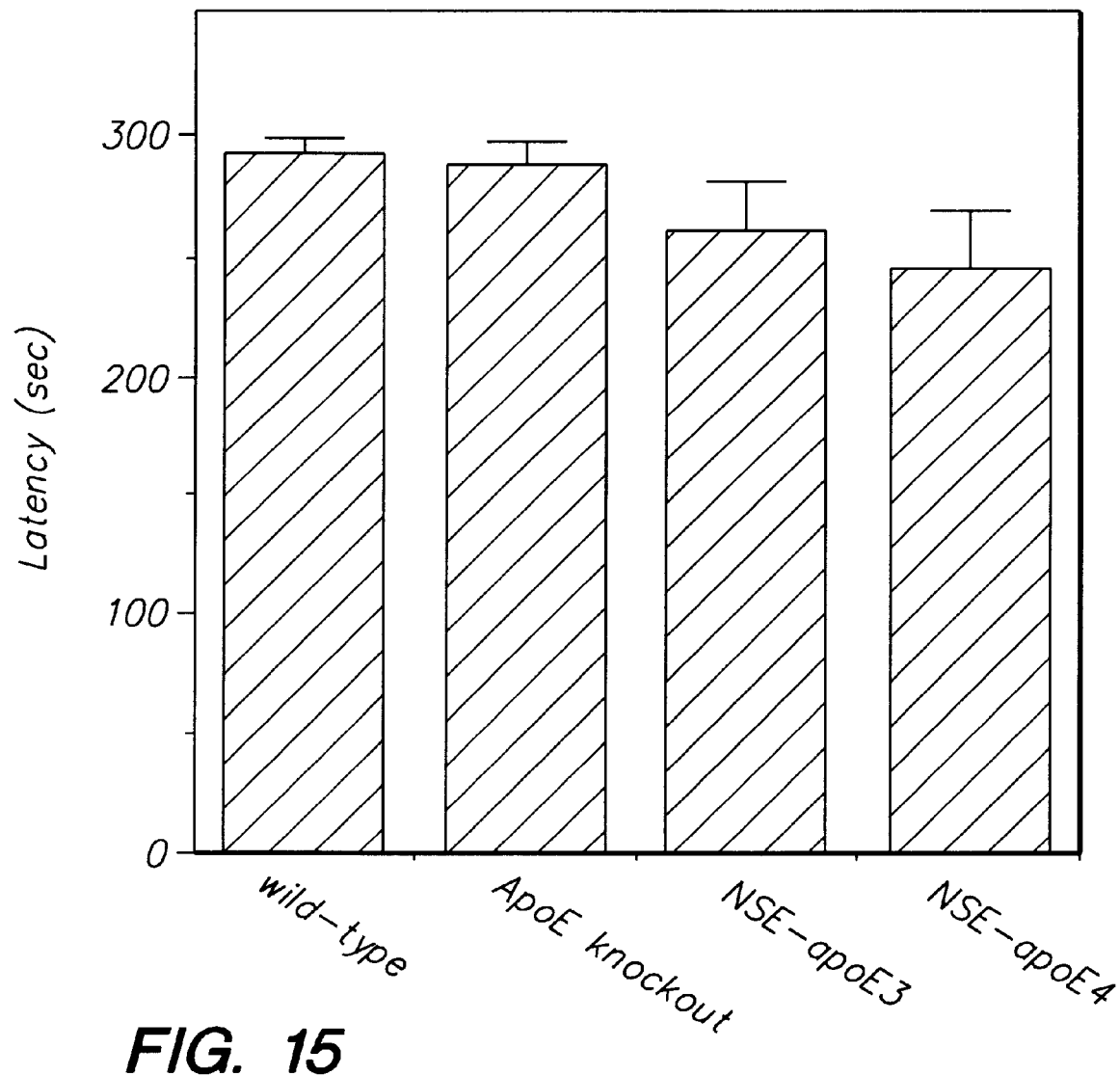
FIG. 15 is a bar graph illustrating time required of the male transgenic mice to reenter a dark compartment following a foot shock 24 hours previously.

The behavioral impairments were specific for spatial learning, as there were no differences within the male or female groups in passive avoidance learning. This test revealed some aspects of gender differences, as more females than males reentered the dark compartment (FIGS. 14 and 15).

WATER MAZE LEARNING

In the water maze test, the ability of the mice to locate a hidden submerged platform in a pool (diameter 61 cm) filled with warm (24° C.) opaque water was tested in two blocks (separated by a 2-hour interval) of two trails each per day for 4 days. Mice that failed to find the platform within 2 minutes were put on it for 15 seconds. The pool was divided into four quadrants. The platform location was changed daily, and the starting point at which the mouse was placed into the water was changed for each trial. On day 5, the ability of the mice to locate a clearly visible platform was tested to exclude differences in vision, swimming speed, and motivation. Time to reach the platform (latency), path length, and swimming speed were recorded with a Noldus Instruments Etho Vision video tracking system set to analyze two samples per second. Because the time required to locate the hidden platform was determined by both path length and swim speed, both parameters were analyzed.

REARING EFFECTS

In mice, body position is detected by the vestibular part of the inner ear, proprioreceptors in joints and muscles, and vision. The two-leg stance during rearing is far less stable than the four-leg stance needed for horizontal movement, and a loss of balance control would be expected to reduce the duration and/or frequency of rearing responses. At 6 months of age, ApoE$^{-/-}$ mice respond normally in tests used to identify vestibular dysfunction, including the reaching, air righting reflex, and swimming.

ApoE$^{-/-}$ mice were also not impaired in motor deficits, indicating that the observed rearing defects were not due to motor deficits. Mice were tested for motor deficits with a rotorod test (San Diego Instruments). After a 1 minute adaptation period on the rod at rest, the rod was accelerated (20 rpm/minute) and the amount of time mice remain on the rod (fall latency) recorded with a fall latency in wild-type and ApoE$^{-/-}$ mice, respectively: females, 38.6±2.7 sec in wild-type versus 54.24±6.7 sec; males, 41.01±4.67 versus 62,27±7.97 sec; n=10–15 mice/group. Between the male groups there were similar, but smaller, differences in rearing events than those observed for the females, without changes in rearing times, active times, or path length (data not shown). These data indicate an important role for apoE, and particularly apoE3, in explorative behavior. The apoE genotype might also cause differential exploratory activity in humans, which could contribute to their (spatial) learning performance.

STATISTICAL ANALYSIS

Comparisons of means between groups or within were assessed by analysis of variance (ANOVA), followed by a Tukey-Kramer posthoc test when appropriate. A probability value of less than 0.05 was considered significant.

In summary, female ApoE$^{-/-}$ mice were found to be impaired in spatial learning and explorative behavior, while their male counterparts were unaffected. These impaired functions were rescued by the introduction of a human apoE3 transgene. A human epoE4 transgene with comparable expression did not rescue such impaired function, demonstrating that apoE plays an isoform-dependent role in cognitive function in the female mouse.

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

We claim:

1. A transgenic mouse comprising:
    (a) genome wherein both alleles of an endogenous apolipoprotein E gene are ablated; and
    (b) a transgene expressing an exogenous human apolipoprotein E3 gene operably linked to a regulatory sequence which directs expression of the exogenous gene in neurons;
    wherein the exogenous human apolipoprotein E3 gene is expressed in said transgenic mouse, and wherein the transgenic mouse displays improved spatial learning and memory in the female compared to a female mouse having no endogenous apolipoprotein E expression.

2. The transgenic mouse of claim 1, wherein the regulatory sequence is a neuron-specific promoter.

3. The transgenic mouse of claim 2, wherein the promoter is rat neuron-specific enolase promoter.

4. An isolated mouse cell comprising:
    (a) a genome wherein both alleles of an endogenous apolipoprotein E gene are ablated; and
    (b) a transgene expressing an exogenous human apolipoprotein E3 gene operably linked to a neuron-specific promoter which directs expression of the exogenous gene in neurons;
    wherein the isolated cell is of neuronal origin.

5. A method of screening for biologically active agents that modulate human apolipoprotein E3, the method comprising:

contacting a candidate agent with a transgenic mouse comprising
(a) a genome wherein both alleles of an endogenous apolipoprotein E gene are ablated; and
(b) a transgene expressing an exogenous human apolipoprotein E3 gene operably linked to a regulatory sequence which directs expression of the exogenous gene in neurons; and
determining the effect of the candidate agent on the transgenic mouse by assessment of behavioral symptoms associated with memory and learning in the transgenic mouse;
wherein agents that modulate apolipoprotein E3 are identified by changes in apolipoprotein E3-mediated behavioral symptoms in the transgenic mouse.

6. The method of claim 5, wherein the behavior differs between mice of different genders.

7. A method of screening for biologically active agents that modulate human apolipoprotein E4, the method comprising:

contacting a candidate agent with a transgenic mouse comprising
(a) a genome wherein both alleles of an endogenous apolipoprotein E gene are ablated; and
(b) a transgene expressing an exogenous human apolipoprotein E4 gene operably linked to a regulatory sequence which directs expression of the exogenous gene in neurons; and
determining the effect of the candidate agent on the transgenic mouse by assessment of behavioral symptoms associated with memory and learning in the transgenic mouse;
wherein agents that modulate apolipoprotein E4 are identified by changes in apolipoprotein E4-mediated behavioral symptoms in the transgenic mouse.

8. A transgenic mouse comprising:
(a) a genome wherein both alleles of an endogenous apolipoprotein E gene are ablated; and
(b) a transgene expressing an exogenous human apolipoprotein E4 gene operably linked to a regulatory sequence which directs expression of the exogenous gene in neurons;
wherein the exogenous human apolipoprotein E4 gene is expressed in said transgenic mouse, and wherein the transgenic mouse displays diminished spatial learning and memory compared to a mouse having no endogenous apolipoprotein E expression.

9. The transgenic mouse of claim 8, wherein the regulatory sequence is a neuron-specific promoter.

10. The transgenic mouse of claim 9, wherein the promoter is rat neuron-specific enolase promoter.

11. An isolated mouse cell comprising:
(a) a genome wherein both alleles of an endogenous apolipoprotein E gene are ablated; and
(b) a transgene expressing an exogenous human apolipoprotein E4 gene operably linked to a neuron-specific promoter which directs expression of the exogenous gene in neurons;
wherein the isolated cell is of neuronal origin.

* * * * *